United States Patent
Kanayama et al.

(10) Patent No.: US 11,337,674 B2
(45) Date of Patent: May 24, 2022

(54) ULTRASONOGRAPHY APPARATUS AND CONTROL METHOD

(71) Applicant: Toshiba Medical Systems Corporation, Otawara (JP)

(72) Inventors: Yuko Kanayama, Nasushiobara (JP); Akihiro Kakee, Nasushiobara (JP); Masaki Watanabe, Shioya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 935 days.

(21) Appl. No.: 14/688,408

(22) Filed: Apr. 16, 2015

(65) Prior Publication Data
US 2015/0297175 A1    Oct. 22, 2015

(30) Foreign Application Priority Data
Apr. 16, 2014 (JP) .............................. JP2014-084967

(51) Int. Cl.
  *A61B 8/00* (2006.01)
  *A61B 8/08* (2006.01)
  *A61B 8/14* (2006.01)

(52) U.S. Cl.
  CPC ................. *A61B 8/14* (2013.01); *A61B 8/485* (2013.01); *A61B 8/5207* (2013.01); *A61B 8/54* (2013.01)

(58) Field of Classification Search
  CPC ......... A61B 8/14; A61B 8/5207; A61B 8/485; A61B 8/54
  See application file for complete search history.

(56) References Cited

U.S. PATENT DOCUMENTS

| 8,758,248 B2 | 6/2014 | Lin et al. |
| 2004/0167403 A1* | 8/2004 | Nightingale ......... A61B 5/0053 600/437 |

(Continued)

FOREIGN PATENT DOCUMENTS

| JP | 2007-75184 A | 3/2007 |
| JP | 2012-115666 A | 6/2012 |

(Continued)

OTHER PUBLICATIONS

Pengfei Song, et al., "Comb-push Ultrasound Shear Elastography (CUSE): A Novel Method for Two-dimensional Shear Elasticity Imaging of Soft Tissues", IEEE Trans. Medical Imaging, vol. 31 (9), 2012, pp. 1-12.

(Continued)

*Primary Examiner* — Patricia J Park
(74) *Attorney, Agent, or Firm* — Oblon, McClelland, Maier & Neustadt, L.L.P.

(57) ABSTRACT

An ultrasonography apparatus includes transmitting circuitry, and processing circuitry. The transmitting circuitry configured to cause an ultrasound probe to transmit a displacement-generation ultrasonic wave to cause a displacement in a tissue of a living body, and cause the probe to transmit an observation ultrasonic wave to observe a displacement of a tissue of a living body in a predetermined scan region, the displacement caused based on the displacement-generation ultrasonic wave. The processing circuitry configured to accept a setting instruction that corresponds to the region, and that is related to an acquisition frequency of an image based on a reflected wave signal that is acquired by the probe by transmission and reception of the observation ultrasonic wave, determine a transmission condition for at least one of the displacement-generation ultrasonic wave and the observation ultrasonic wave, according to the setting (Continued)

| SCAN MODE | NUMBER OF PUSH-PULSE FOCUS | PUSH-PULSE TRANSMISSION INTERVAL [cm] | OBSERVATION-PULSE TRANSMISSION INTERVAL [mm] |
|---|---|---|---|
| SUCCESSIVE SCAN MODE (HIGH SPEED) | 1 | 1.5 | 1.5 |
| SUCCESSIVE SCAN MODE (MEDIUM SPEED) | 1 | 1 | 1 |
| SUCCESSIVE SCAN MODE (LOW SPEED) | 2 | 1.5 | 1.5 |
| ONE SHOT MODE | 2 | 0.6 | 0.5 | instruction, and control the transmission circuitry based on the condition.

19 Claims, 18 Drawing Sheets

(56) References Cited

U.S. PATENT DOCUMENTS

| | | | | |
|---|---|---|---|---|
| 2008/0081993 | A1* | 4/2008 | Waki | A61B 5/02007 |
| | | | | 600/438 |
| 2013/0123630 | A1* | 5/2013 | Freiburger | G01S 7/52042 |
| | | | | 600/443 |
| 2013/0131511 | A1* | 5/2013 | Peterson | G01S 7/52042 |
| | | | | 600/438 |
| 2013/0245442 | A1* | 9/2013 | Hazard | A61B 8/485 |
| | | | | 600/438 |
| 2013/0317361 | A1 | 11/2013 | Tabaru et al. | |
| 2014/0330125 | A1* | 11/2014 | Snyder | A61B 8/14 |
| | | | | 600/444 |
| 2015/0272547 | A1* | 10/2015 | Freiburger | A61B 8/54 |
| | | | | 600/438 |

FOREIGN PATENT DOCUMENTS

| | | | |
|---|---|---|---|
| JP | 2013-512026 A | 4/2013 | |
| JP | WO 2013047380 A1 * | 4/2013 | ........... A61B 8/0841 |
| JP | 2014-28029 A | 2/2014 | |
| WO | WO 2012/105152 A1 | 8/2012 | |

OTHER PUBLICATIONS

Thomas Deffieux, et al., "On the Effects of Reflected Waves in Transient Shear Wave Elastography", IEEE Transactions on Ultrasonics, Ferroelectrics, and Frequency Control, vol. 58, (10), 2011, p. 2032.

Japanese Office Action dated Oct. 17, 2017 in Japanese Patent Application No. 2014-084967.

Japanese Office Action dated Jan. 9, 2018 in Japanese Patent Application No. 2014-084967, 3 pages.

* cited by examiner

FIG.3

| SCAN MODE | PUSH-PULSE TRANSMISSION MODE | PUSH-PULSE TRANSMISSION INTERVAL [cm] | OBSERVATION-PULSE TRANSMISSION INTERVAL [mm] |
|---|---|---|---|
| SUCCESSIVE SCAN MODE (HIGH SPEED) | ONE SIDE | 1.5 | 1.5 |
| SUCCESSIVE SCAN MODE (MEDIUM SPEED) | ONE SIDE | 1 | 1 |
| SUCCESSIVE SCAN MODE (LOW SPEED) | ONE SIDE | 0.6 | 0.5 |
| ONE SHOT MODE | BOTH SIDES | 0.6 | 0.5 |

| SCAN MODE | NUMBER OF PUSH-PULSE FOCUS | PUSH-PULSE TRANSMISSION INTERVAL [cm] | OBSERVATION-PULSE TRANSMISSION INTERVAL [mm] |
|---|---|---|---|
| SUCCESSIVE SCAN MODE (HIGH SPEED) | 1 | 1.5 | 1.5 |
| SUCCESSIVE SCAN MODE (MEDIUM SPEED) | 1 | 1 | 1 |
| SUCCESSIVE SCAN MODE (LOW SPEED) | 2 | 1.5 | 1.5 |
| ONE SHOT MODE | 2 | 0.6 | 0.5 |

FIG.10

| MOVEMENT OF ULTRASOUND PROBE | FRAME RATE [fps] |
|---|---|
| FAST | 1.5 |
| INTERMEDIATE | 1 |
| SLOW | 0.5 |

FIG.13

| B-MODE S/N RATIO | FRAME RATE [fps] |
|---|---|
| HIGH | 1.5 |
| INTERMEDIATE | 1 |
| LOW | 0.5 |

FIG.15

| DISPLACEMENT AMOUNT | FRAME RATE [fps] |
|---|---|
| LARGE | 1.5 |
| MEDIUM | 1 |
| SMALL | 0.5 | derive
ULTRASONOGRAPHY APPARATUS AND CONTROL METHOD

CROSS-REFERENCE TO RELATED APPLICATIONS

This application is based upon and claims the benefit of priority from Japanese Patent Application No. 2014-84967, filed on Apr. 16, 2014, the entire contents of all of which are incorporated herein by reference.

FIELD

Embodiments described herein relate generally to an ultrasonography apparatus and a control method.

BACKGROUND

Conventionally, a technique called elastography has been known in which the stiffness of a tissue of a living body is measured, and a distribution of measured stiffness is visualized. Elastography is used for diagnosis of diseases in which the stiffness of a tissue varies according to stages of development of a lesion such as cirrhosis, for example. In elastography, as for methods of evaluating the stiffness by causing a displacement in a tissue, there are following two main methods.

The first method is a method of visualizing relative stiffness based on a degree of distortion at each point that is observed in a scanning section when pressure is applied to and released from a tissue through a body surface by an ultrasound probe. The second method is a method in which a displacement based on shear waves is caused in a tissue by applying acoustic radiation force or mechanical vibration to the tissue through a body surface, and a displacement at each point in a scanning section is observed over time, thereby acquiring the propagation speed of shear waves to acquire the elastic modulus. In the former method, the degree of a local displacement is dependent on the scale of manually moving an ultrasound prove, and it is assessed whether a region of interest is relatively hard or soft when compared with a region therearound. On the other hand, in the latter method, the absolute elastic modulus of a region of interest can be acquired.

In the latter method, when a stiffness image showing the stiffness of a tissue is generated, push pulses that are focused ultrasound pulses with a high sound pressure are used as an acoustic radiation force. When shear waves are generated by this push pulse, various transmission conditions are set. Therefore, an operator sets various transmission conditions one by one.

BRIEF DESCRIPTION OF THE DRAWINGS

FIG. 3 shows one example of data stored in a transmission-condition storage unit according to the first embodiment;

FIG. 10 shows one example of data stored in a frame-rate storage unit according to the second embodiment;

FIG. 13 shows one example of data stored in a frame-rate storage unit according to the third embodiment;

FIG. 15 shows one example of data stored in a frame-rate storage unit according to a modification of the third embodiment;

DETAILED DESCRIPTION

An ultrasonography apparatus according to embodiments includes transmitting circuitry, and processing circuitry. The transmitting circuitry configured to cause an ultrasound probe to transmit a displacement-generation ultrasonic wave to cause a displacement in a tissue of a living body based on an acoustic radiation force, and cause the ultrasound probe to transmit an observation ultrasonic wave to observe a displacement of a tissue of a living body in a predetermined scan region, the displacement caused based on the displacement-generation ultrasonic wave. The processing circuitry configured to accept a setting instruction that corresponds to the predetermined scan region, and that is related to an acquisition frequency of an image based on a reflected wave signal that is acquired by the ultrasound probe by transmission and reception of the observation ultrasonic wave, determine a transmission condition for at least one of the displacement-generation ultrasonic wave and the observation ultrasonic wave, according to the setting instruction, and control the transmission circuitry based on the transmission condition.

First Embodiment

Figure 1:
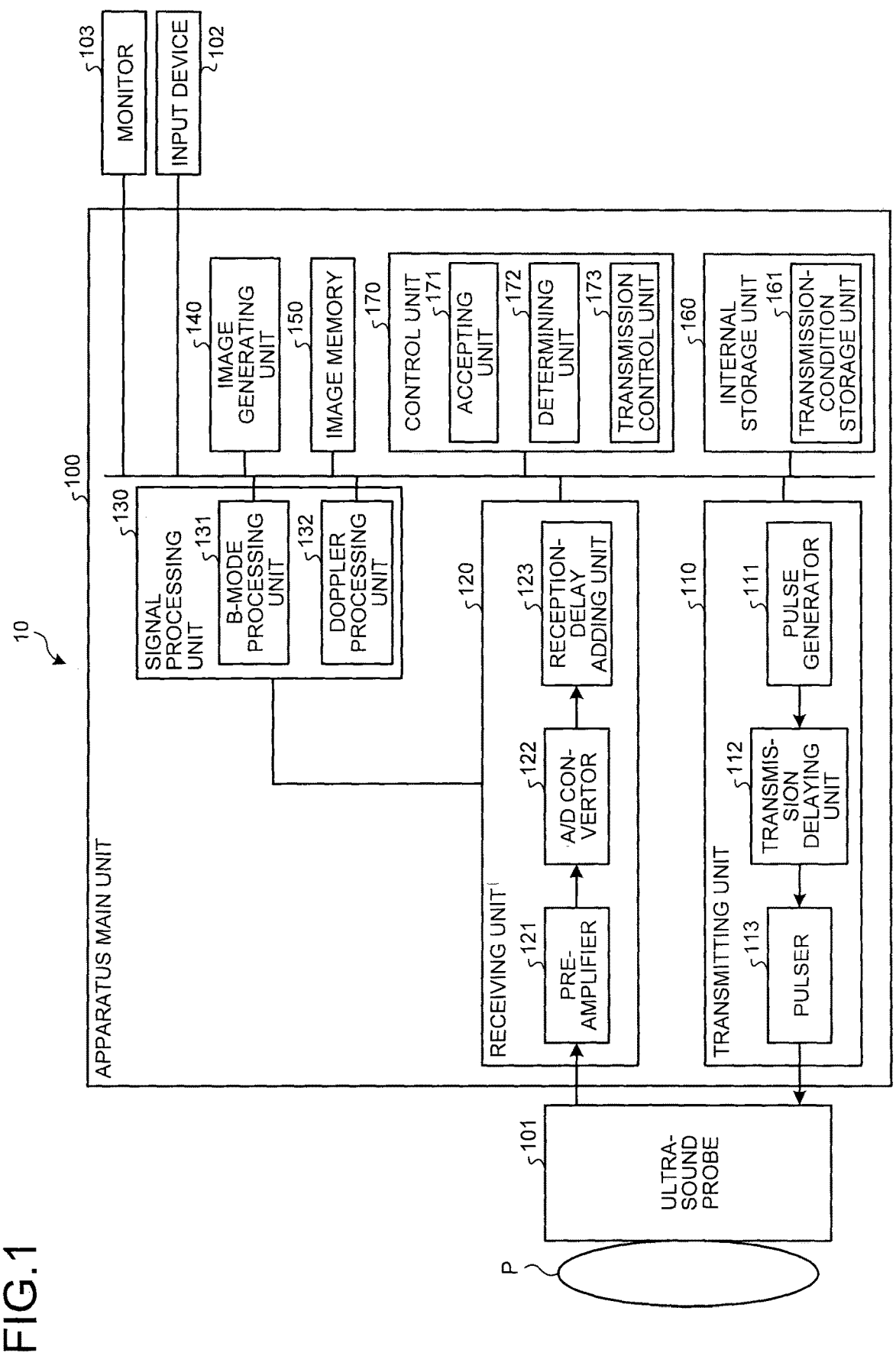
FIG. 1 is a block diagram showing a configuration example of an ultrasonography apparatus according to a first embodiment.

FIG. 1 is a block diagram showing a configuration example of an ultrasonography apparatus 10 according to a first embodiment. As shown in FIG. 1, the ultrasonography apparatus 10 includes an apparatus main unit 100, an ultrasound probe 101, an input device 102, and a monitor 103.

The ultrasound probe 101 includes multiple transducers (for example, piezoelectric transducers), and these transducers generate ultrasonic waves based on a driving signal that is supplied by a transmitting unit 110 described later included in the apparatus main unit 100. Moreover, the transducers included in the ultrasound probe 101 receive a reflected wave from a subject P and convert into an electric signal. Furthermore, the ultrasound probe 101 includes a matching layer that is provided for the transducer, a backing material to prevent propagation of an ultrasonic wave to a backward direction from the transducer, and the like.

When ultrasonic waves are transmitted to the subject P from the ultrasound probe 101, the ultrasonic waves are sequentially reflected on a discontinuous surface of an acoustic impedance in a tissue of the subject P, and received by the transducers included in the ultrasound probe 101 as reflected wave signals. The amplitude of the received reflected wave signals is dependent on a difference in the acoustic impedance on the discontinuous surface on which the ultrasonic waves are reflected. Reflected wave signals when transmitted ultrasonic wave pulses are reflected on a surface of a moving bloodstream, a cardiac wall, and the like have frequency shifts dependent on a velocity component of a moving body relative to a direction of transmission of ultrasonic waves by the Doppler effect.

The first embodiment is applicable to any of a case in which the ultrasound probe 101 shown in FIG. 1 is a one-dimensional ultrasound probe in which multiple piezoelectric transducers are arranged in a single row, a case of a one-dimensional ultrasound probe in which multiple piezoelectric transducers are arranged in a single row are mechanically swung, and a case of a two-dimensional ultrasound probe in which multiple piezoelectric transducers are arranged two-dimensionally in a lattice.

The input device 102 includes a mouse, a keyboard, a button, a panel switch, a touch command screen, a foot switch, a track ball, and a joy stick, and the like, and accepts various kinds of setting requests from an operator of the ultrasonography apparatus 10, an transfers the accepted various kinds of setting requests to the apparatus main unit 100.

The monitor 103 displays, for example, a graphical user interface (GUI) for an operator of the ultrasonography apparatus 10 to input various kinds of setting requests by using the input device 102, or displays ultrasonic image data generated in the apparatus main unit 100, and the like.

The apparatus main unit 100 includes an apparatus that generates ultrasonic image data based on a reflected wave signal received by the ultrasound probe 101, and includes the transmitting unit 110, a receiving unit 120, a signal processing unit 130, an image generating unit 140, an image memory 150, an internal storage unit 160, and a control unit 170 as shown in FIG. 1.

The transmitting unit 110 controls the transmission directivity in transmission of an ultrasonic wave. For example, the transmitting unit 110 includes a pulse generator 111, a transmission delaying unit 112, and a pulser 113, and provides a driving signal to the ultrasound probe 101. The pulse generator 111 generates rate pulses to form transmission ultrasonic waves repeatedly at a predetermined rate frequency (pulse repetition frequency (PRF)). The rate pulse applies a voltage to the pulser 113 in a state in which various transmission delay times are given thereto by passing through the transmission delaying unit 112. That is, the transmission delaying unit 112 gives a transmission delay time for each transducer that is required to converge ultrasonic waves generated by the ultrasound probe 101 into a beam form and to determine the transmission directivity to each rate pulse generated by the pulse generator 111. The pulser 113 applies a driving signal (driving pulse) to the ultrasound probe 101 at timing based on the rate pulse. The transmission direction or the transmission delay time is stored in the internal storage unit 160 described later, and the transmitting unit 110 refers to the internal storage unit 160 to control the transmission directivity.

The driving pulse is transferred to the transducer inside the ultrasound probe 101 through a cable from the pulser 113, and then converted into a mechanical vibration from an electrical signal by the transducer. This mechanical vibration is transmitted as ultrasonic wave inside a living body. Ultrasonic waves having various transmission delay times each of which differs for every transducer are converged to be propagated in a predetermined direction. The transmission delaying unit 112 varies transmission delay times to be given to the respective rate pulses, to adjust the transmission direction from a surface of the transducer arbitrarily. The transmitting unit 110 controls the number and a position (transmission aperture) of the transducers to be used to transmit an ultrasonic beam, and a transmission delay time according to a position of each of the transducers structuring the transmission aperture, to give the transmission directivity. For example, the transmission delaying unit 112 gives a transmission delay time to each rate pulse that is generated by the pulse generator 111, thereby controlling the position of a focus (transmission focus) in a depth direction in transmission of an ultrasonic wave.

The transmitting unit 110 has a function enabling to change a transmission frequency, a transmission driving voltage, and the like instantaneously to execute a predetermined scan sequence based on an instruction of the control unit 170 described later. Particularly, a change of the transmission driving voltage is achieved by a linear-amplifier transmission circuitry that can change the value instantaneously, or a mechanism of electrically switching multiple power supply units.

After reaching the transducer inside the ultrasound probe 101, a reflected wave of an ultrasonic wave transmitted by the ultrasound probe 101 is converted into an electrical signal (reflected wave signal) from mechanical vibration by the transducer, and is then input to the receiving unit 120.

The receiving unit 120 controls the reception directivity in reception of an ultrasonic wave. For example, the receiving unit 120 includes a preamplifier 121, an analog/digital (A/D) convertor 122, and a reception-delay adding unit 123, and generates reflected wave data by performing various kinds of processing on a reflected wave signal received by the ultrasound probe 101. The preamplifier 121 performs gain correction processing by amplifying a reflected wave signal per channel. The A/D convertor 122 performs A/D conversion of the reflected wave signal subjected to the gain correction. The reception-delay adding unit 123 gives a reception delay time that is required to determine the reception directivity, per channel, and adds reflected wave signals (digital signals) to which reception delay times are given, to generate reflected wave data. By this addition processing, a reflection component from a direction according to the reception directivity of the reflected wave signal is emphasized. The reception direction or the reception delay time is stored in the internal storage unit 160 described later, and the receiving unit 120 refers to the internal storage unit 160 to control the reception directivity. The receiving unit 120 according to the first embodiment is also capable of performing parallel simultaneous reception.

The signal processing unit 130 performs various kinds of signal processing on reflected wave data that is generated from a reflected wave signal by the receiving unit 120. For example, the signal processing unit 130 includes a B-mode processing unit 131, and a Doppler processing unit 132.

The B-mode processing unit 131 generates data (B-mode data) in which a signal intensity is expressed by the intensity of brightness for each sample point, by performing logarithm amplification, envelope detection processing, and the like on the reflected wave data received by the receiving unit 120.

The Doppler processing unit 132 generates data (Doppler data) in which movement information of a moving body is extracted based on the Doppler effect from the reflected wave data received from the receiving unit 120. Specifically, the Doppler processing unit 132 generates Doppler data in which an average speed, a dispersion value, a power value, and the like are extracted at each sample point as the movement information of a moving body. The moving body is, for example, blood stream, a tissue of cardiac wall, and a contrast agent.

The image generating unit 140 generates ultrasonic image data from the data that is generated by the signal processing unit 130. The image generating unit 140 generates B-mode image data in which the intensity of a reflected wave is expressed by brightness, from B-mode data generated by the signal processing unit 130. Furthermore, the image generating unit 140 generates Doppler image data that indicates moving body information, from Doppler data generated by the signal processing unit 130. The Doppler image data is speed image data, dispersion image data, power image data, or image data in which these are combined.

Generally, the image generating unit 140 converts (scan converts) a scan-line signal string of ultrasonic scanning into a scan-line signal string of a video format represented by television and the like, to generate ultrasonic image data for display. Specifically, the image generating unit 140 generates the ultrasonic image data for display by performing coordinate transformation according to a scanning form of an ultrasonic wave by the ultrasound probe 101. Moreover, the image generating unit 140 performs image processing (smoothing) to regenerate a brightness average-value image, image processing (edge enhancement) using a differential filter in an image, and the like as various kinds of image processing other than the scan conversion, by using image frames after scan conversion, for example. Furthermore, the image generating unit 140 composites supplementary information (character information of various kinds of parameters, scales, body marks, and the like) with the ultrasonic image data.

That is, the B-mode data and the Doppler data are the ultrasonic image data before performing the scan conversion processing, and data generated by the image generating unit 140 is ultrasonic image data for display after the scan conversion processing. The image generating unit 140 generates volume data by performing coordinate transformation according to a scanning form of an ultrasonic wave by the ultrasound probe 101 when the signal processing unit 130 generates three-dimensional data (three-dimensional B-mode data and three-dimensional Doppler data). The image generating unit 140 then performs various kinds of rendering processing on the volume data to generate two-dimensional image data for display.

The image memory 150 is a memory that stores image data for display generated by the image generating unit 140. Moreover, the image memory 150 can also store data generated by the signal processing unit 130. B-mode data and Doppler data stored in the image memory 150 can be retrieved, for example, by an operator after diagnosis, and are to be ultrasonic image data for display through the image generating unit 140.

The internal storage unit 160 stores a control program to perform image processing and display processing, diagnosis information (for example, patient identification (ID), observations of a doctor, and the like), or various kinds of data such as a diagnosis protocol and various kinds of body marks. Moreover, the internal storage unit 160 is also used to archive image data stored in the image memory 150, and the like as necessary. Furthermore, data stored in the internal storage unit 160 can be transferred to an external device through an interface unit not shown.

Moreover, the internal storage unit 160 stores a transmission-condition storage unit 161. The transmission-condition storage unit 161 is described later.

The control unit 170 controls overall processing of the ultrasonography apparatus. Specifically, the control unit 170 controls processing of the transmitting unit 110, the receiving unit 120, the signal processing unit 130, and the image generating unit 140 based on various kinds of setting requests input by an operator through the input device 102, or various kinds of control programs and various kinds of data read from the internal storage unit 160. Furthermore, the control unit 170 controls to display ultrasonic image data for display that is stored in the image memory 150 on the monitor 103.

Moreover, the control unit 170 includes an accepting unit 171, a determining unit 172, and a transmission control unit 173. The accepting unit 171, the determining unit 172, and the transmission control unit 173 are described later.

Note that the transmitting unit 110, the receiving unit 120, and the like can be configured with hardware of a processor (central processing unit (CPU), a micro-processing unit (MPU), an integrated circuitry, and the like), and can be configured with a program that is formed into modules as software.

The ultrasonography apparatus 10 according to the first embodiment is an apparatus that can measure the stiffness of a tissue of a living body, and can perform elastography in which distribution of the measured stiffness is visualized. Specifically, the ultrasonography apparatus 10 according to the first embodiment is an apparatus that can perform elastography by causing a displacement in a tissue of a living body by applying an acoustic radiation force.

That is, the transmitting unit 110 according to the first embodiment causes the ultrasound probe 101 to transmit push pulses to cause a displacement in a tissue of a living body based on an acoustic radiation force. The transmitting unit 110 according to the first embodiment causes the ultrasound probe 101 to generate observation pulses to observe a displacement in a tissue of a living body occurring based on the push pulses in a predetermined scan region. The observation pulses are transmitted to observe a propagation speed of shear waves that are generated by the push pulses at each sample point in a scan region. Generally, the observation pulse is transmitted multiple times (for example, 100 times) to each scan line in a scan region. The receiving unit 120 generates reflected wave data from a reflected wave signal of the observation pulse that is transmitted to each scan line in a scan region. The push pulse is one example of a displacement-generation ultrasonic wave. Moreover, the observation pulse is one example of an observation ultrasonic wave. Furthermore, the scan region signifies a region that is scanned for forming an image, and corresponds to, for example, a region of interest (ROI).

Subsequently, the Doppler processing unit 132 observes changes of a displacement over time at each sample point. For example, the Doppler processing unit 132 performs auto-correlation processing of reflected wave data of the observation pulse. Thus, the Doppler processing unit 132 generates movement information (tissue Doppler data) over multiple time phases at each of multiple sample points of each scan line. The Doppler processing unit 132 then time integrates speed components of the tissue Doppler data of multiple time phases that are acquired at each of the sample points of each scan line. Thus, the Doppler processing unit 132 acquires changes of a displacement over time at each sample point by calculating displacements of each of the sample points of each scan line over multiple time phases. These changes of a displacement over time can be drawn as a plot in which a horizontal axis is an elapsed time and a vertical axis is a displacement. The Doppler processing unit 132 stores the calculated changes of a displacement over time at each sample point in the image memory 150. In the above case, the observation pulse is a transmission pulse for tissue Doppler.

The image generating unit 140 then generates stiffness image data in which the stiffness of a tissue of a living body is expressed by colors, from the changes of a displacement over time at each sample point in a scan region. For example, the image generating unit 140 calculates, from correlation of plots of changes of displacements over time at sample points adjacent to each other at the same depth, arrival times of shear waves by acquiring an amount of difference when the similarity of the plots is the highest. The image generating unit 140 then calculates a propagation speed of a shear wave (hereinafter, "shear speed") at each sample point from a difference in arrival times of respective sample points in an azimuth direction, and from a position of each sample. Subsequently, the image generating unit 140 allocates a pixel value (color map) according to a shear speed to each sample point in the scan region, thereby generating shear-speed image data that corresponds to the size of the scan region. Note that the shear speed is high in a hard tissue, and the shear speed is low in a soft tissue. In other words, a value of the shear speed is a value that indicates the stiffness (elastic modulus) of a tissue. That is, the image generating unit 140 generates the shear-speed image data as stiffness image data that indicates the stiffness of a tissue of a living body. The image generating unit 140 may calculate the arrival time of a shear wave described above based on time when a displacement is the largest at each sample point.

The image generating unit 140 may calculate the Young's modulus or the elastic shear modulus from the shear speed, and generate stiffness image data based on the calculated Young's modulus or the elastic shear modulus. Either of the shear speed, the Young's modulus, and the elastic shear modulus can be used as a physical amount that expresses the stiffness of a tissue of a living body. In the following, a case in which the image generating unit 140 uses the shear speed as a physical amount that expresses the stiffness of a tissue of a living body is explained.

When a stiffness image is generated by elastography using push pulses, an operator of the ultrasonography apparatus 10 is to be setting various transmission conditions.

Figure 2A:
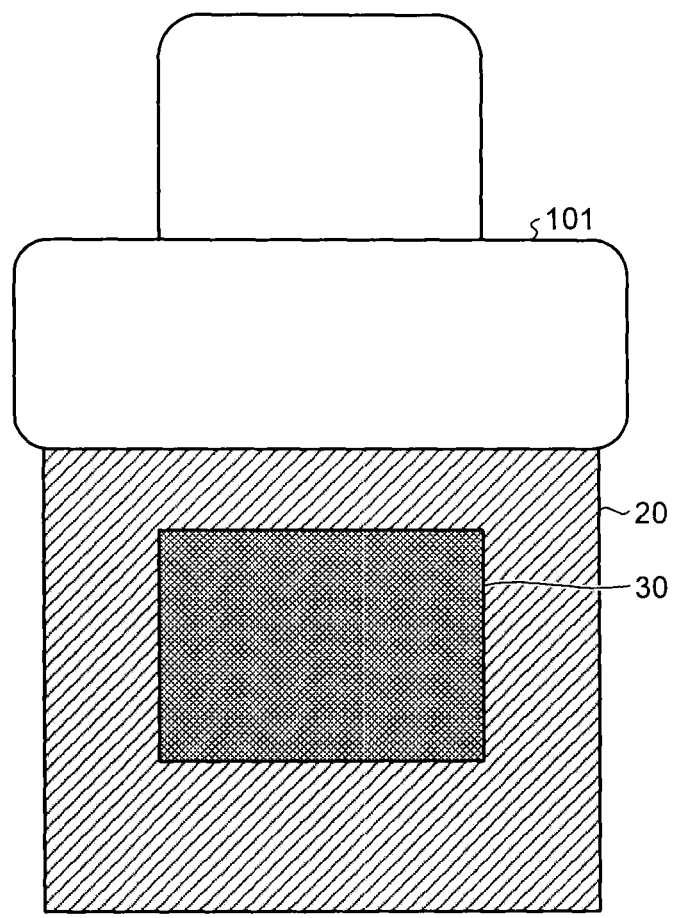
FIGS. 2A to 2D are diagrams for explaining transmission conditions.
Figure 2B:
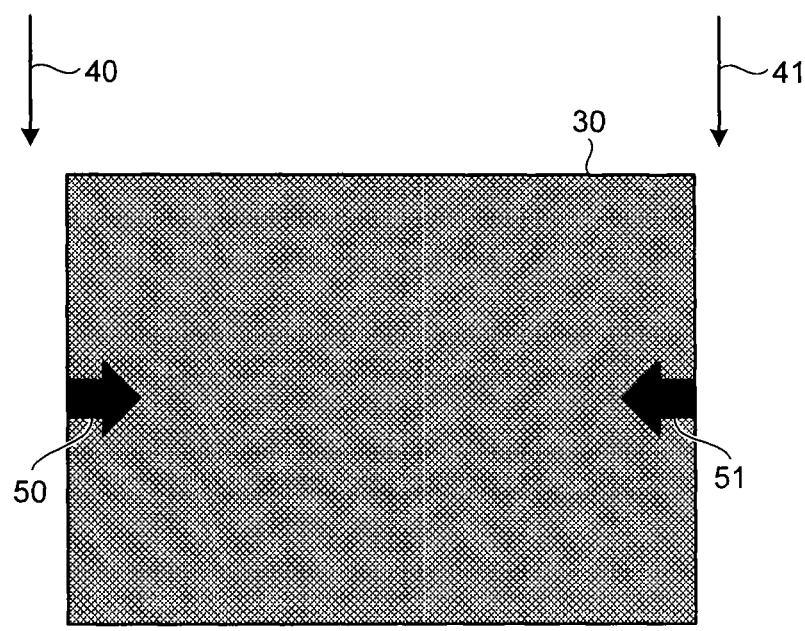
Figure 2C:
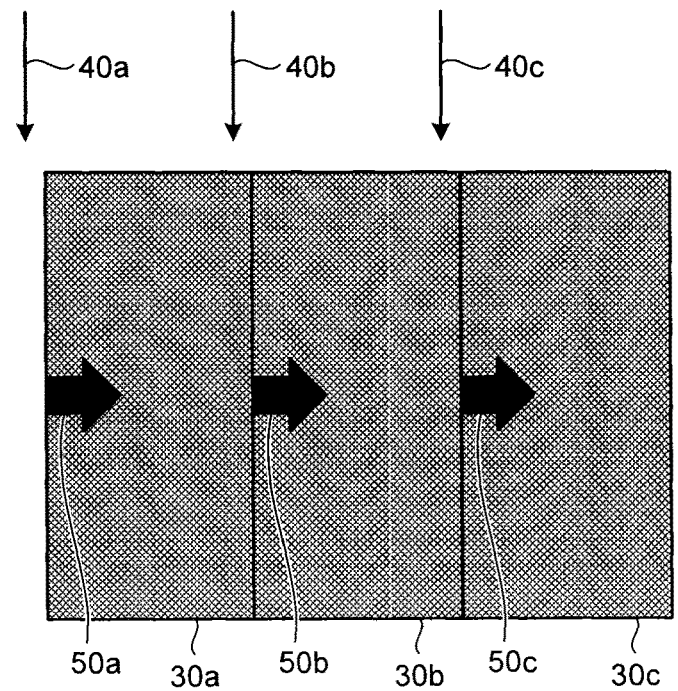
Figure 2D:
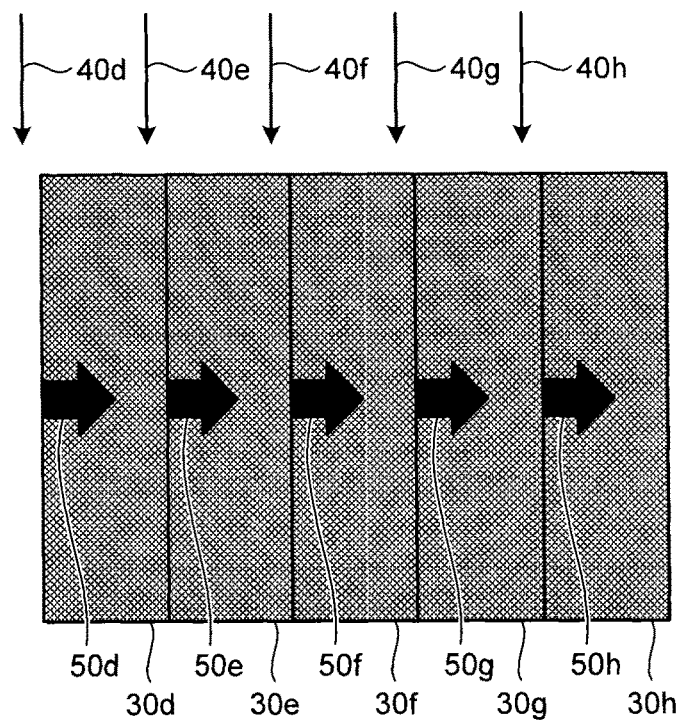

FIG. 2A to FIG. 2D are diagrams for explaining transmission conditions. For example, as shown in FIG. 2A, when elastography is performed, an operator switches a display mode of the ultrasonography apparatus 10 to a display mode to perform elastography (for example, called elastomode). In this elastomode, B-mode pulses are repeatedly transmitted and received except when processing to display a stiffness image is performed, and a B-mode image 20 is displayed on the monitor 103 in a substantially real time. For example, viewing this B-mode image 20, the operator operates the ultrasound probe 101 to set a region of interest (ROI) 30 for which a stiffness image is to be displayed to a position at which a stiffness image is wished to be displayed (for example, a position at which a portion considered as a tumor is displayed). When the operator inputs a scan start instruction to instruct start of scanning, the ultrasonography apparatus 10 generates a stiffness image of the ROI 30. In this case, for example, a transmission condition are set as shown in FIG. 2B to FIG. 2D.

In FIG. 2B, for example, a case in which whether to transmit push pulses to one end of the ROI 30, or to transmit push pulses to both ends is set as a transmission condition is explained. When push pulses are transmitted to one end, for example, the ultrasonography apparatus 10 transmits push pulses to a transmission position 40, and observes shear waves that propagate in a direction of an arrow 50 by these push pulses. On the other hand, when push pulses are transmitted to both ends of the ROI 30, the ultrasonography apparatus 10 also observes shear waves that propagate in a direction of an arrow 51 by the push pulses transmitted to a transmission position 41, in addition to the shear waves by the push pulses transmitted to the transmission position 40. The ultrasonography apparatus 10 then calculates the shear speeds of the shear waves that propagate in both directions in the ROI 30, and acquires more accurate shear speed by integrating values of respective sample points. Therefore, generally, to enhance the image quality, it is preferable to transmit push pulses to both ends of the ROI 30, and to increase a frame rate, it is preferable to transmit push pulses to one end of the ROI 30.

To transmit push pulses to both ends of the ROI 30 is effective when regions having different stiffness are present in a subject. This is because shear waves reflect at a boundary of regions having different stiffness and interfere with each other, and observation of the shear waves is difficult. To reduce the influence of this reflection, application of a filter to remove a component of a shear wave that propagates in an inverse direction to the direction of shear waves to be observed has been proposed. However, the influence of the reflection is not necessarily reduced completely by this filter. Therefore, by observing the respective shear waves that propagate in the both directions, regions in which the shear waves are likely to reflect are shifted from each other, and by superimposing respective observation results, a highly reliable stiffness image is generated.

Furthermore, in FIG. 2C and FIG. 2D, a case in which intervals in the azimuth direction of push pulses are set as a transmission condition is explained. The reason why the intervals in the azimuth direction of push pulses are set is because shear waves generated by transmission of push pulses attenuate as propagation. Therefore, by transmitting push pulses at predetermined intervals from multiple transmission positions, a range observed by a single push pulse transmission can be narrowed. For example, in an example shown in FIG. 2C, three transmission positions 40a, 40b, and 40c are set, and in an example shown in FIG. 2D, five transmission positions 40d, 40e, 40f, 40g, and 40h are set. In the case of FIG. 2C, the transmission frequency of push pulses can be decreased compared to the case of FIG. 2D, and therefore, it is suitable for a case of increasing a frame rate; however, there is a possibility that shear waves attenuate at a right end of respective divided ROIs 30a, 30b, and 30c. On the other hand, in the case of FIG. 2D, the intervals of the respective transmission positions are narrower than those of the case of FIG. 2D, and therefore, it is suitable for a case of enhancing the image quality; however, high-speed visualization is difficult because the transmission frequency of push pulses increases.

Moreover, the ultrasonography apparatus 10 is required to comply with acoustic power regulations. Because a push pulse used in elastography has larger acoustic power compared to, for example, a B-mode transmission waveform, generated heat is also high. To reduce the heat to be within a range of the regulations, for example, the acoustic power per single push pulse is lowered (that is, to lower the sound pressure, or to shorten the irradiation time), or the transmission frequency of push pulses per unit time is reduced. Because the acoustic power of a transmitted push pulse has correlation with a displacement amount of a tissue of a living body generated by the push pulse, if the acoustic power of the push pulse is lowered, a sufficient amount of displacement for observation cannot be caused, and shear waves cannot be observed clearly. Therefore, for high-speed visualization, when the transmission frequency is reduced maintaining the acoustic power, rather than the acoustic power is lowered maintaining the transmission frequency of push pulses, the image quality can be enhanced as a result.

As described, in elastography, various transmission conditions are set to cause a sufficient amount of displacement for observation to perform visualization. These transmission conditions are not necessarily defined uniquely, but differ according to desired image quality or frame rate. Therefore, it is difficult for an operator to set optimal transmission conditions one by one at each imaging. In addition, for example, when a frame rate is wished to be changed, an operator is required to re-set a transmission condition each time the frame rate is changed, and this requires time and effort.

Therefore, the ultrasonography apparatus 10 according to the first embodiment enables to acquire a stiffness image with high image quality by a simple operation, by having a configuration explained below.

The transmission-condition storage unit 161 according to the first embodiment stores transmission conditions. For example, the transmission-condition storage unit 161 stores the transmission conditions according to a one shot mode in which imaging is performed for a single time, and a successive scan mode in which images are generated repeatedly at a predetermined frame rate.

FIG. 3 shows one example of data stored in the transmission-condition storage unit 161 according to the first embodiment. As shown in FIG. 3, the transmission-condition storage unit 161 stores data in which a "scan mode", a "push-pulse transmission mode", a "push-pulse transmission interval" and an "observation-pulse transmission interval" are associated with each other. The data stored in the transmission-condition storage unit 161 may be registered by an operator in advance, or be preset.

The "scan mode" is data indicating a mode in which scanning is performed. For example, in the "scan mode", whether the "one shot mode" in which imaging is performed for a single time or the "successive scan mode" in which imaging is performed repeatedly in the elastomode is registered. The "successive scan mode" is registered as multiple modes in which frame rates for imaging a scan region are different from each other. For example, as the "successive scan mode", a "successive scan mode (high speed)", a "successive scan mode (medium speed)", and a "successive scan mode (low speed)" are registered. Among these, the "successive scan mode (high speed)" is a scan mode in which the frame rate is higher than the other successive scan modes. Moreover, the "successive scan mode (low speed)" is a scan mode in which the frame rate is lower than the other successive scan modes. Furthermore, the "successive scan mode (medium speed)" is a scan mode in which the frame rate is set to an intermediate level between the "successive scan mode (high speed)" and the "successive scan mode (low speed)".

Moreover, the "push-pulse transmission mode" is data indicating whether a transmission position to which push pulses are transmitted is on "one side" or on "both sides". For example, the push-pulse transmission mode "one side" indicates that push pulses are transmitted to one end of a scan region in a corresponding scan mode. Furthermore, the push-pulse transmission mode "both sides" indicates that push pulses are transmitted to both ends of a scan region in a corresponding scan mode. When this push-pulse transmission mode is "one side", the direction of shear waves that propagate by push pulses is a single direction, and when "both sides", two directions.

Moreover, the "push-pulse transmission interval" is data indicating intervals in the azimuth direction of push pulses that are transmitted to a scan region. For example, the push-pulse transmission interval "1 centimeter (cm)" indicates that push pulses are transmitted at "1 cm" intervals to the ROI 30 specified by an operator.

Furthermore, the "observation-pulse transmission interval" is data that indicates intervals in the azimuth direction of observation push pulses that are transmitted to a scan region. For example, the observation-pulse transmission interval "1 millimeter (mm)" indicates that the observation pulses are transmitted at "1 mm" intervals to the ROI 30 specified by an operator.

FIG. 3 only shows one example. For example, although the push-pulse transmission interval and the observation-pulse transmission interval are indicated by "distances" in FIG. 3, embodiments are not limited thereto. For example, the push-pulse transmission interval and the observation-pulse transmission interval may be indicated by "angles". As a specific example, it is preferable that when the ultrasound probe 101 is a linear probe, the push-pulse transmission interval and the observation-pulse transmission interval be indicated by "distances", and when the ultrasound probe 101 is a convex probe, the push-pulse transmission interval and the observation-pulse transmission interval be indicated by "angles". Moreover, for example, the transmission-condition storage unit 161 is not required to store all of the items, the push-pulse transmission mode, the push-pulse transmission interval, and the observation-pulse transmission interval described above as transmission conditions, and may store other items. Furthermore, for example, when the push-pulse transmission mode is "one side", specifically to which side (right side or left side) out of two ends of a scan region, transmission is performed may be stored.

The accepting unit 171 accepts various kinds of instructions, and outputs accepted instructions to other processing units as appropriate. Moreover, the accepting unit 171 makes various kinds of settings according to accepted instructions.

For example, the accepting unit 171 sets the ROI 30. As one example, the accepting unit 171 causes the monitor 103 to display a GUI for ROI setting, and accepts an instruction to set the ROI 30 made by an operator on the GUI for ROI setting. Subsequently, the accepting unit 171 sets the ROI 30 based on the accepted instruction.

Furthermore, the accepting unit 171 according to the first embodiment accepts an instruction to set a scan mode. For example, the accepting unit 171 accepts either one of instructions out of the instructions to set the "successive scan mode (high speed)", the "successive scan mode (medium speed)", the "successive scan mode (low speed)", and the "one shot mode" from an operator through the input device 102. The accepting unit 171 outputs an accepted instruction to the determining unit 172.

Although a case in which the accepting unit 171 accepts an instruction to set a scan mode is explained in the first embodiment, embodiments are not limited thereto. For example, the accepting unit 171 may accept an instruction to set a frame rate from an operator. This is because the scan mode (one shot mode, successive scan mode) in the present embodiment practically signifies a frame rate. For example, to the "successive scan mode (high speed)", the "successive scan mode (medium speed)", and the "successive scan mode (low speed)", frame rates different from each other are set. As one example, the frame rate of the "successive scan mode (high speed)" is "1.5 frame per second (fps)", the frame rate of the "successive scan mode (medium speed)" is "1 fps", and the frame rate of the "successive scan mode (low speed)" is "0.5 fps". In this case, the accepting unit 171 accepts an instruction to set the image acquisition frequency corresponding to a scan region in a predetermined period.

Moreover, in the "one shot mode", a pause time (cooling time) is set. This pause time is a period that is set to cool the temperature of a tissue of a living body that has risen by scanning (transmission and reception of push pulses and observation pulses). As one example, after scanning in the "one shot mode", it is set to be in a freeze state for five seconds. This means the same as that the frame mode of the "one shot mode" is set to "0.2 fps". That is, it can be regarded that the accepting unit 171 accepts an instruction to set the image acquisition frequency (once) corresponding to a scan region during a predetermined period (pause time).

That is, in the ultrasonography apparatus 10 according to the first embodiment, the accepting unit 171 accepts an instruction to set an image acquisition frequency corresponding to a predetermined time. When the accepting unit 171 accepts an instruction to set a frame rate, the transmission-condition storage unit 161 stores a transmission condition according to the frame rate. For example, the transmission-condition storage unit 161 data in which the frame rate "1 fps", the push-pulse transmission mode "one side", the push-pulse transmission interval "1 cm", and the observation-pulse transmission interval "1 mm" are associated with each other. In other words, the accepting unit 171 accepts a setting instruction relating to the image acquisition frequency based on reflected wave signals that are collected by the ultrasound probe by transmission and reception of observation pulses, corresponding to a predetermined scan region.

The determining unit 172 according to the first embodiment determines a transmission condition according to the instruction accepted by the accepting unit 171. For example, the determining unit 172 accepts, from the accepting unit 171, an instruction to set a scan mode input by an operator. The determining unit 172 then refers to the transmission-condition storage unit 161, and determines a transmission condition according to the accepted instruction. Subsequently, the determining unit 172 outputs the determined transmission condition to the transmission control unit 173.

For example, when the instruction to set the "successive scan mode (medium speed)" is accepted from the accepting unit 171, the determining unit 172 refers to the transmission-condition storage unit 161. The determining unit 172 then acquires the push-pulse transmission mode "one side", the push-pulse transmission interval "1 cm", and the observation-pulse transmission interval "1 mm" that are associated with the "successive scan mode (medium speed)". Subsequently, the determining unit 172 determines the respective acquired items as the transmission condition.

Furthermore, for example, when an instruction to set the "one shot mode" is accepted, the determining unit 172 refers to the transmission-condition storage unit 161. The determining unit 172 then acquires the push-pulse transmission mode "both sides", the push-pulse transmission interval "0.6 cm", and the observation-pulse transmission interval "0.5 mm" that are associated with the "one shot mode". Subsequently, the determining unit 172 determines the respective acquired items as the transmission condition.

The transmission control unit 173 according to the first embodiment controls the transmitting unit 110 based on the transmission condition. For example, the transmission control unit 173 calculates application voltages of the push pulse and the observation pulse based on the determined transmission condition. The transmission control unit 173 then performs stiffness-image generation processing based on the calculated application voltages of the push pulse and the observation pulse, and the transmission condition.

Figure 4A:
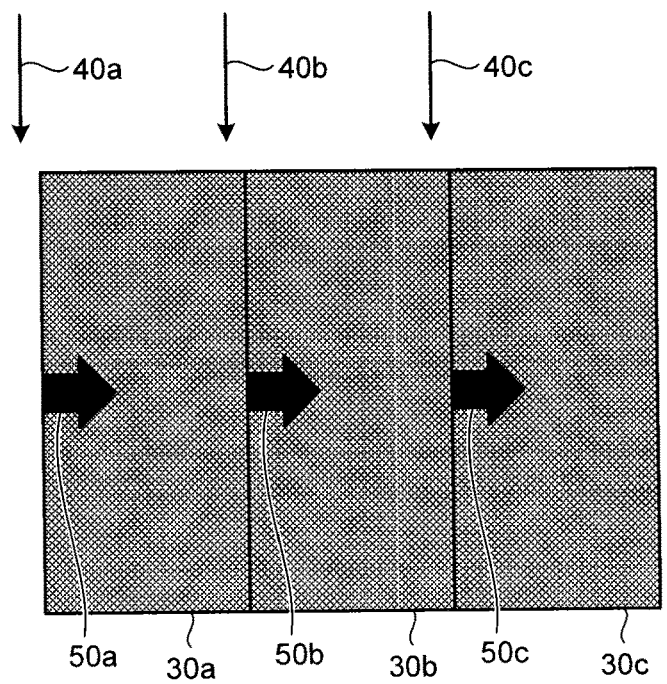
FIGS. 4A and 4B are diagrams for explaining processing performed by a transmission control unit according to the first embodiment.
Figure 4B:
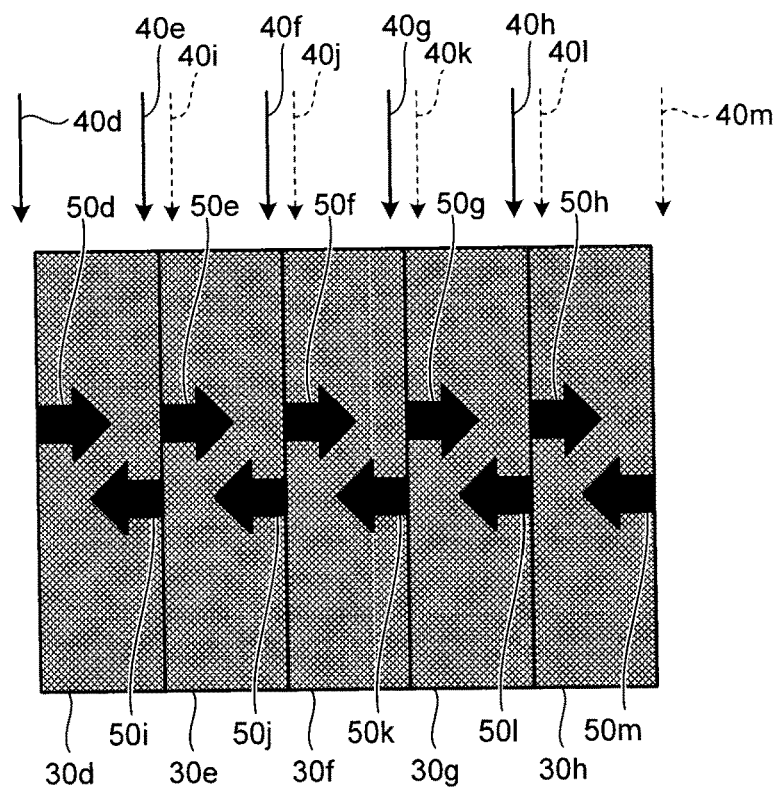

FIG. 4A and FIG. 4B are diagrams for explaining processing performed by the transmission control unit 173 according to the first embodiment. In FIG. 4A, a case of generating stiffness image data of the ROI 30 in the "successive scan mode (medium speed)" is exemplified, and in FIG. 4B, a case of generating stiffness image data of the ROI 30 in the "one shot mode" is exemplified. In FIG. 4A and FIG. 4B, a case in which the number of simultaneous reception of the ultrasound probe 101 is 4 lines is explained.

First, a case of generating stiffness image data of the ROI 30 in the "successive scan mode (medium speed)" is explained using FIG. 4A. In this case, the push-pulse transmission mode "one side", the push-pulse transmission interval "1 cm", and the observation-pulse transmission interval "1 mm" have already been determined as the transmission condition by processing of the determining unit 172. Regions obtained by equally dividing the ROI 30 in the azimuth direction as respective divided ROIs 30a, 30b, and 30c are hereinafter expressed as divided ROIs.

The transmission control unit 173 calculates the transmission frequencies of the push pulse and the observation pulse that is required to perform a single time of imaging (capturing) based on the determined transmission condition. For example, the transmission control unit 173 calculates the transmission frequency of the observation pulse required to observe the divided ROI 30a first. In this case, the transmission control unit 173 acquires "10 lines (=1 cm/1 mm)" as the number of transmission lines (scan lines) of the observation pulse because the observation-pulse transmission interval is "1 mm" and the push-pulse transmission interval is "1 cm". For example, when the observation pulse is transmitted 100 times for a single scan line, the transmission control unit 173 acquires "1000 times (=10 lines×100 times)" as the transmission frequency of the observation pulse required to observe the divided ROI 30a.

Subsequently, the transmission control unit 173 calculates the transmission frequency of the push pulse that is required to observe the divided ROI 30a. In this case, the transmission control unit 173 acquires "3 times" as the transmission frequency of the push pulse required to observe the divided ROI 30a because the transmission frequency (number of scan lines) of the observation pulse required to observe the divided ROI 30a is "10 lines" and the simultaneous reception lines are 4 lines. Specifically, out of 10 scan lines, the first push pulse is transmitted to observe the first to the fourth scan lines to observe the first to the fourth scan lines, the second push pulse is transmitted to observe the fifth to the eighth scan lines, and the third push pulse is transmitted to observe the ninth and the tenth scan lines.

Subsequently, the transmission control unit 173 calculates the transmission frequency of the push pulse and the observation pulse that is required to observe the respective divided ROIs 30b and 30c. In an example shown in FIG. 4A, the transmission conditions of the push pulse and the observation pulse for the divided ROIs 30b and 30c are the same as that of the divided ROI 30a. Therefore, the transmission control unit 173 similarly acquires "3 times" as the transmission frequency of the push pulse and "1000 times" as the transmission frequency of the observation pulse for the divided ROIs 30b and 30c also.

The transmission control unit 173 then sums the calculated transmission frequencies of the push pulse and the observation pulse that are required to observe the respective divided ROIs 30a, 30b, and 30c. Thus, the transmission control unit 173 acquires the transmission frequency "9 times" of the push pulse and the transmission frequency "3000 times" of the observation pulse that are required to perform single imaging.

As described, the transmission control unit 173 calculates the transmission frequency of the push pulse and the transmission frequency of the observation pulse required to perform a single time of imaging. The transmission control unit 173 then calculates application voltages for the push pulse and the observation pulse based on the calculated transmission frequency of the push pulse and the transmission frequency of the observation pulse.

For example, the transmission control unit 173 calculates the application voltages of the push pulse and the observation pulse based on a mechanical index (MI) value and a thermal index (TI) value. In the internal storage unit 160, for example, an MI value and a heating amount when the push pulse and the observation pulse are irradiated one time each are stored. When the push pulse and the observation pulse are transmitted within a range in which the TI value does not exceed the regulated value, the transmission control unit 173 calculates a heating amount per unit time (average heating amount) based on the heating amount of heat generated when the push pulse and the observation pulse are transmitted one time each, the transmission frequency of the push pulse and the transmission frequency of the observation pulse, and the frame rate. The transmission control unit 173 acquires the highest voltage within a range in which this average heating amount does not exceed the regulated value as the application voltage for the push pulse and the observation pulse.

Subsequently, the transmission control unit 173 causes the transmitting unit 110 to transmit the push pulse and the observation pulse using the calculated application voltages of the push pulse and the observation pulse. For example, to visualize the ROI 30 once, the transmission control unit 173 first controls to transmit the push pulse at a transmission position 40a, and observes a shear wave that propagates in the direction indicated by an arrow 50a in the divided ROI 30a (controls to transmit and receive the observation pulse). Next, the transmission control unit 173 controls to transmit the push pulse at a transmission position 40b, and observes a shear wave that propagates in the direction indicated by an arrow 50b in the divided ROI 30b. Subsequently, the transmission control unit 173 controls to transmit the push pulse at the transmission position 40c, and observes a shear wave that propagates in the direction indicated by an arrow 50c in the divided ROI 30c. Thus, the stiffness image data of the ROI 30 is generated based on changes of a displacement over time at each sample point observed in each of the divided ROIs 30a, 30b, and 30c.

Next, a case of generating stiffness image data of the ROI 30 in the "one shot mode" is explained using FIG. 4B. In this case, the push pulse transmission mode "both sides", the push-pulse transmission interval "0.6 cm", and the observation-pulse transmission interval "0.5 mm" has already been determined as the transmission condition by processing of the determining unit 172.

The transmission control unit 173 calculates the transmission frequencies of the push pulse and the observation pulse that is required to perform a single time of imaging based on the determined transmission condition. In this case, the transmission control unit 173 acquires "12 lines (=0.6 cm/0.5 mm)" as the number of the transmission lines (scan lines) of the observation pulse that is required to observe a divided ROI 30d because the observation-pulse transmission interval is "0.5 mm" and the push-pulse transmission interval is "0.6 cm". For example, when the observation pulse is transmitted 100 times for a single scan line, the transmission control unit 173 acquires "2400 times (=12 lines×100 times×2 (both sides))" as the transmission frequency of the observation pulse required to observe the divided ROI 30d. Because the push-pulse transmission mode is "both sides", a value of the transmission frequency is doubled.

Subsequently, the transmission control unit 173 calculates the transmission frequency of the push pulse that is required to observe the divided ROI 30d. In this case, the transmission control unit 173 acquires "6 times" as the transmission frequency of the push pulse required to observe the divided ROI 30d because the number of transmission lines (number of scan lines) of the observation pulse required to observe the divided ROI 30d is "12 lines" and the simultaneous reception lines are 4 lines.

Subsequently, the transmission control unit 173 calculates the transmission frequencies of the push pulse and the observation pulse that are required to observe the respective divided ROIs 30e, 30f, 30g, and 30h. In an example shown in FIG. 4B, the transmission conditions of the push pulse and the observation pulse for the divided ROIs 30e, 30f, 30g, and 30h are the same as that of the divided ROI 30d. Therefore, the transmission control unit 173 similarly acquires "6 times" as the transmission frequency of the push pulse and "2400 times" as the transmission frequency of the observation pulse for the respective divided ROIs 30e, 30f, 30g, and 30h also.

The transmission control unit 173 then sums the calculated transmission frequencies of the push pulse and the observation pulse that are required to observe the respective divided ROIs 30d, 30e, 30f, 30g, and 30h. Thus, the transmission control unit 173 acquires the transmission frequency "30 times" of the push pulse and the transmission frequency "12000 times" of the observation pulse that are required to perform single imaging.

As described, the transmission control unit 173 calculates the transmission frequency of the push pulse and the transmission frequency of the observation pulse required to perform a single time of imaging. The transmission control unit 173 then calculates application voltages for the push pulse and the observation pulse based on the calculated transmission frequency of the push pulse and the transmission frequency of the observation pulse.

For example, the transmission control unit 173 calculates the application voltages of the push pulse and the observation pulse based on the MI value and the TI value. This processing is the same as that in the case of FIG. 4A, and therefore, explanation thereof is omitted.

Subsequently, the transmission control unit 173 causes the transmitting unit 110 to transmit the push pulse and the observation pulse using the calculated application voltages of the push pulse and the observation pulse. For example, to image the ROI 30 once, the transmission control unit 173 first controls to transmit the push pulse at a transmission position 40d, and observes a shear wave that propagates in the direction indicated by an arrow 50d in the divided ROI 30d. Next, the transmission control unit 173 controls to transmit the push pulse at a transmission position 40e, and observes a shear wave that propagates in the direction indicated by an arrow 50e in the divided ROI 30e. Subsequently, the transmission control unit 173 controls to transmit the push pulse at the transmission position 40f, and observes a shear wave that propagates in the direction indicated by an arrow 50f in the divided ROI 30f. Subsequently, the transmission control unit 173 controls to transmit the push pulse at the transmission position 40g, and observes a shear wave that propagates in the direction indicated by an arrow 50g in the divided ROI 30g. Subsequently, the transmission control unit 173 controls to transmit the push pulse at the transmission position 40h, and observes a shear wave that propagates in the direction indicated by an arrow 50h in the divided ROI 30h. The transmission control unit 173 then controls to transmit the push pulse at a transmission position 40i, and observes a shear wave that propagates in the direction indicated by an arrow 50i in the divided ROI 30d. The transmission control unit 173 then controls to transmit the push pulse at a transmission position 40j, and observes a shear wave that propagates in the direction indicated by an arrow 50j in the divided ROI 30e. The transmission control unit 173 then controls to transmit the push pulse at a transmission position 40k, and observes a shear wave that propagates in the direction indicated by an arrow 50k in the divided ROI 30f. The transmission control unit 173 then controls to transmit the push pulse at a transmission position 40l, and observes a shear wave that propagates in the direction indicated by an arrow 50l in the divided ROI 30g. The transmission control unit 173 then controls to transmit the push pulse at a transmission position 40m, and observes a shear wave that propagates in the direction indicated by an arrow 50m in the divided ROI 30h. Thus, shear waves that propagate in both directions are observed in each of the divided ROIs 30d, 30e, 30f, 30g, and 30h, and the stiffness image data of the ROI 30 is generated based on changes of a displacement over time at each observed sample.

As described, the transmission control unit 173 performs control to cause the transmitting unit 110 to transmit the push pulse and the observation pulse based on a transmission condition. Thus, stiffness image data is finally generated.

Figure 5:
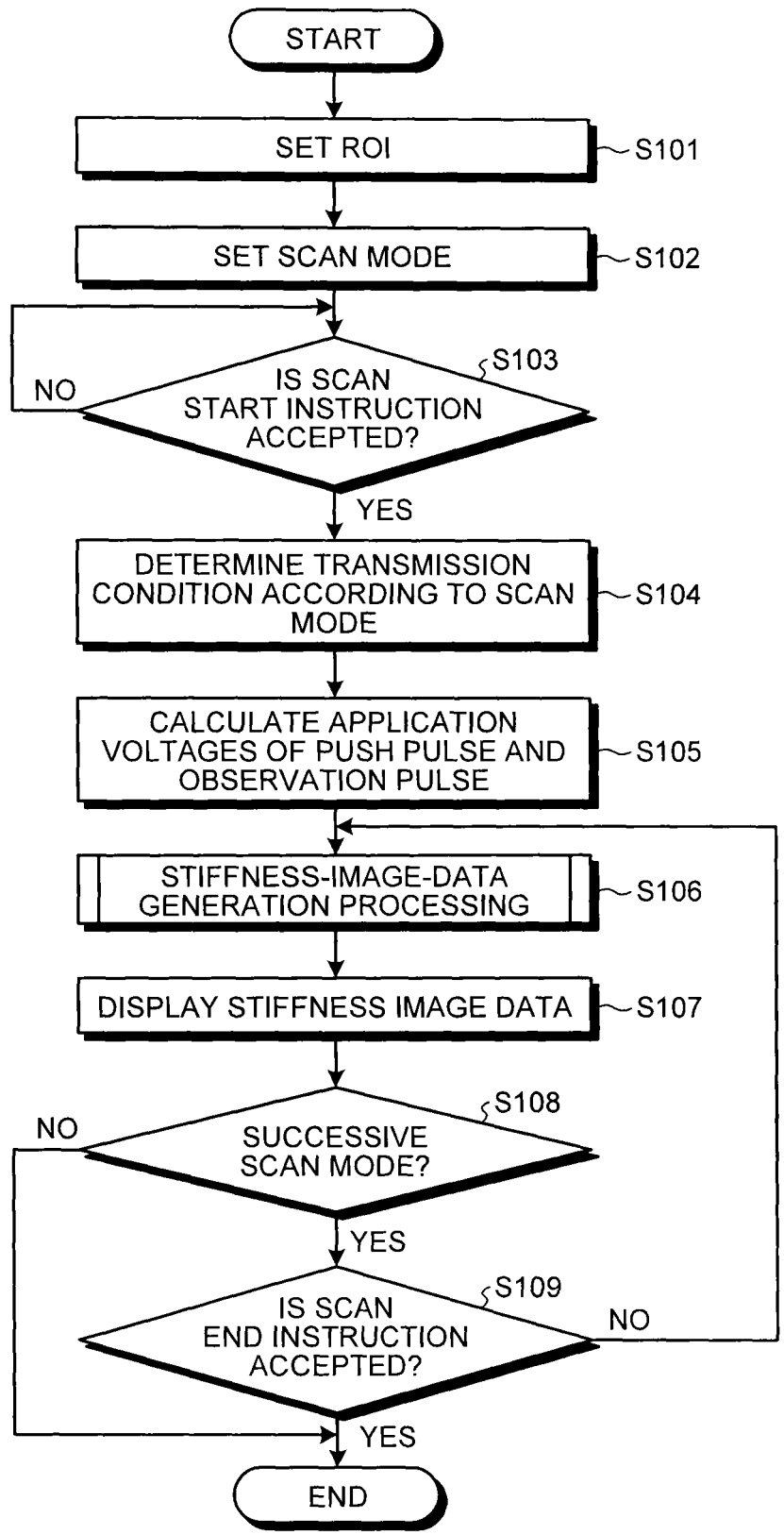
FIG. 5 is a flowchart of a processing procedure of the ultrasonography apparatus according to the first embodiment.

FIG. 5 is a flowchart of a processing procedure of the ultrasonography apparatus 10 according to the first embodiment. The processing procedure exemplified in FIG. 5 corresponds to a processing procedure after switched to the elastomode by an operator.

As shown in FIG. 5, in the ultrasonography apparatus 10 according to the first embodiment, when switched to the elastomode, the accepting unit 171 accepts an instruction to set the ROI 30, and sets the ROI 30 according to the accepted instruction (step S101).

Subsequently, the accepting unit 171 accepts an instruction to set a scan mode (step S102). For example, the accepting unit 171 accepts either one of instructions to set to the "successive scan mode (high speed)", the "successive scan mode (medium speed)", the "successive scan mode (low speed)", or the "one shot mode" from an operator. The accepting unit 171 then outputs the accepted instruction to set a scan mode to the determining unit 172.

When the accepting unit 171 accepts a scan start instruction to start scanning (imaging) (step S103: YES), the determining unit 172 determines a transmission condition according to the scan mode accepted by the accepting unit 171 (step S104). For example, the determining unit 172 accepts, from the accepting unit 171, the instruction to set a scan mode input by an operator. The determining unit 172 then refers to the transmission-condition storage unit 161, and determines a transmission condition according to the accepted instruction. The determining unit 172 then outputs the determined transmission condition to the transmission control unit 173. Note that the determining unit 172 waits in standby until a scan start instruction is accepted by the accepting unit 171 (step S103: NO).

Subsequently, the transmission control unit 173 calculates application voltages of the push pulse and the observation pulse (step S105). The transmission control unit 173 then performs stiffness-image-data generation processing based on the calculated application voltages of the push pulse and the observation pulse, and on the transmission condition (step S106).

Figures 6, 7:
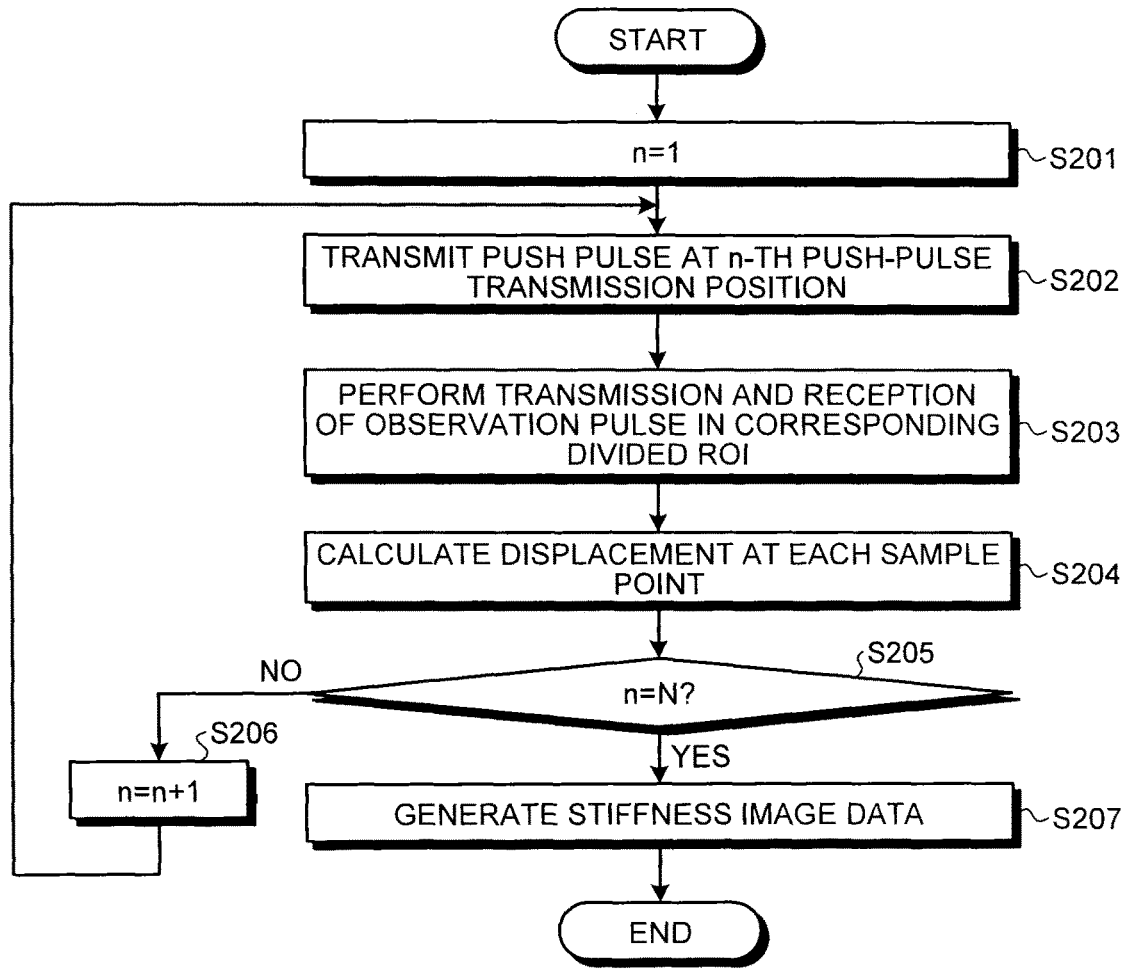
FIG. 6 is a flowchart of a processing procedure of a stiffness-image-data generation processing.
FIG. 7 shows one example of data stored in a transmission-condition storage unit according to a modification of the first embodiment.

The stiffness-image-data generation processing at step S106 in FIG. 5 is explained herein using FIG. 6. FIG. 6 is a flowchart of a processing procedure of the stiffness-image-data generation processing.

As shown in FIG. 6, the transmission control unit 173 sets "n=1" (step S201). This "n" indicates a number of a push-pulse transmission position that is set to observe a displacement at each sample point by transmitting the push pulse at all of the push-pulse transmission positions. That is, the transmission control unit 173 keeps incrementing "n" by 1 each until the number of the push-pulse transmission position reaches "N", thereby transmitting the push pulse at all of the push-pulse transmission positions to observe a displacement at each sample point.

Subsequently, by control by the transmission control unit 173, the transmitting unit 110 transmits the push pulse from the ultrasound probe 101 at the n-th push-pulse transmission position (step S202). Then, by control by the transmitting unit 110 and the receiving unit 120, the ultrasound probe 101 performs transmission and reception of the observation pulse in a divided ROI corresponding to the push pulse (step S203). Subsequently, the image generating unit 140 calculates a displacement at each sample point in the divided ROI (step S204).

For example, in the example shown in FIG. 4A, the transmitting unit 110 transmits push pulses in the sequence of the transmission positions 40a, 40b, and 40c. Every time a push pulse is transmitted at the respective transmission positions 40a, 40b, and 40c, the ultrasound probe 101 performs transmission and reception of the observation pulse at the respective divided ROIs 30a, 30b, and 30c, and the image generating unit 140 calculates displacements. Moreover, in the example shown in FIG. 4B, the transmitting unit 110 transmits push pulses in the sequence of the transmission positions 40d, 40e, 40f, 40g, 40h, 40i, 40j, 40k, 40l, and 40m. Every time a push pulse is transmitted at the respective transmission positions 40d, 40e, 40f, 40g, 40h, 40i, 40j, 40k, 40l, and 40m, the ultrasound probe 101 performs transmission and reception of the observation pulse in the respective divided ROIs 30d, 30e, 30f, 30g, and 30h, and the image generating unit 140 calculates displacements. When the number of scan lines in the observed divided ROI 30 is more than the number of simultaneous reception lines of the ultrasonography apparatus 10, transmission of the push pulse is repeated at the n-th transmission position until displacements are calculated for all of the scan lines. Specifically, when the number of scan lines in the divided ROI 30 is "10 lines" and the number of simultaneous reception lines is "4 lines", the transmission control unit 173 controls to repeat the processing from step S202 to step S204 for three times.

The transmission control unit 173 then determines whether "n=N" (step S205). When "n=N" is not satisfied (step S205: NO), the transmission control unit 173 increments "n" by 1 (step S206), and shifts to the processing at step S202.

On the other hand, when "n=N" (step S205: YES), the transmission control unit 173 generates stiffness-image data based on changes of displacements over time at all sample points (step S207).

Returning back to explanation of FIG. 5, by control by the transmission control unit 173, the monitor 103 displays the stiffness image data of the ROI 30 (step S107).

When the specified scan mode is a successive scan mode (step S108: YES), the transmission control unit 173 shifts to step S106 and repeats generating stiffness image data until a scan end instruction is accepted (step S109: NO).

On the other hand, when the scan end instruction is accepted (step S109: YES), the transmission control unit 173 ends generation of stiffness image data.

Moreover, when it is not in successive scan mode (step S108: NO), that is, when it is in the one shot mode, the transmission control unit 173 ends generation of stiffness image data. At this time, the transmission control unit 173 controls to be in a freeze state (state in which processing to start scanning is not accepted) during a pause period from the end of scanning.

Note that the processing procedure described above is just one example. For example, as described above, the accepting unit 171 may perform the processing to accept an instruction to set a scan mode (step S102) and the processing to accept a scan start instruction (step S103) separately, or may perform these processing as one processing. For example, the accepting unit 171 can accept an instruction to set a scan mode and a scan start instruction as one instruction, by accepting an instruction to start scan in the one shot mode, or by accepting an instruction to start scan in a successive scan mode as a single scan start instruction.

Furthermore, for example, in the ultrasonography apparatus 10, the processing to accept an instruction to set a scan mode (step S102) may be performed prior to the processing to set the ROI 30 (step S101).

As described above, in the ultrasonography apparatus 10 according to the first embodiment, the accepting unit 171 accepts an instruction to set the frequency of acquiring images corresponding to a scan region in a predetermined period. The determining unit 172 determines a transmission condition according to the instruction accepted by the accepting unit 171. The transmission control unit 173 performs control to cause the transmitting unit 110 to transmit the push pulse and the observation pulse based on the determined transmission condition.

For example, in the ultrasonography apparatus 10, the transmission-condition storage unit 161 stores optimal transmission conditions according to a scan mode or to a frame rate. Therefore, accepting an instruction to set a scan mode, or an instruction to set a frame rate from an operator, the ultrasonography apparatus 10 can determine an optimal transmission condition according to the accepted instruction. By this arrangement, the ultrasonography apparatus 10 according to the first embodiment enables to acquire a high quality stiffness image by a simple operation.

Although a case in which the accepting unit 171 accepts either one out of the "successive scan mode (high speed)", the "successive scan mode (medium speed)", the "successive scan mode (low speed)", and the "one shot mode" from an operator through the input device 102 has been explained in the present embodiment, the number of scan itself when scan of an entire scan region is counted as one time may be regarded as an instruction to set the scanning frequency. In other words, the accepting unit 171 may accept an instruction to set only the frequency of acquiring images corresponding to a scan region regardless of a period.

Modification of the First Embodiment

Furthermore, in addition to the transmission condition described above, the ultrasonography apparatus 10 according to the first embodiment may determine the number of push-pulse focuses.

FIG. 7 shows one example of data stored in the transmission-condition storage unit according to a modification of the first embodiment. As shown in FIG. 7, the transmission-condition storage unit 161 stores the number of push-pulse focuses as a transmission condition. This number of push-pulse focuses indicates the number of focuses of the push pulse that is transmitted to a scan region.

Figure 8:
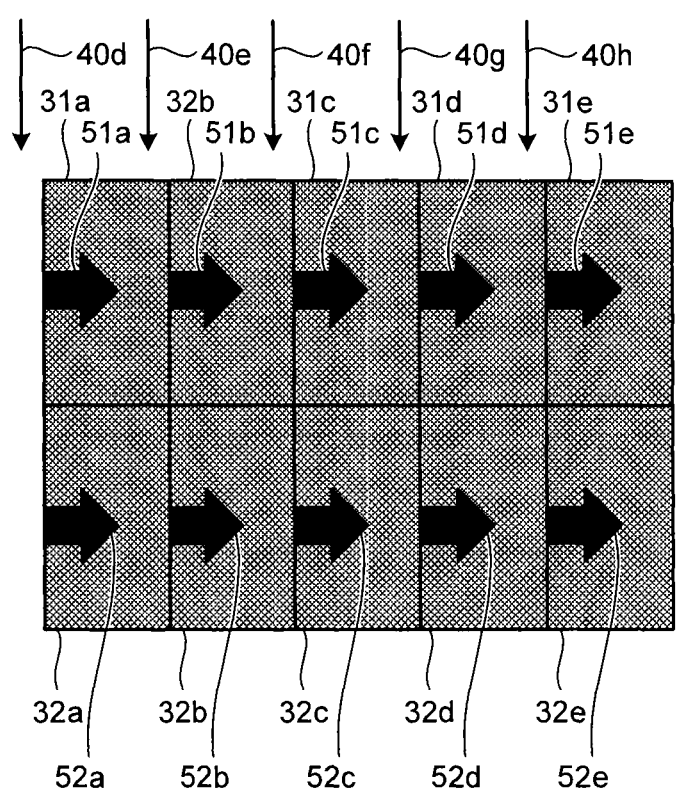
FIG. 8 shows one example of a transmission condition according to the modification of the first embodiment.

FIG. 8 shows one example of a transmission condition according to the modification of the first embodiment. In FIG. 8, a case in which the one shot mode is specified in the transmission-condition storage unit 161 is explained. In this case, for example, the determining unit 172 acquires the number of push-pulse focuses "2", the push-pulse transmission interval "0.6 cm", and the observation-pulse transmission interval "0.5 mm" that are associated with the "one shot mode".

In this case, for example, as shown in FIG. 8, to perform imaging of the ROI 30 one time, the transmission control unit 173 controls to transmit the push pulse that is focused on a divided ROI 31a at the transmission position 40d, and observes a shear wave that propagates in the direction indicated by an arrow 51a in the divided ROI 31a. The transmission control unit 173 controls to transmit the push pulse that is focused on a divided ROI 32a at the transmission position 40d, and observes a shear wave that propagates in the direction indicated by an arrow 52a in the divided ROI 32a. The transmission control unit 173 controls to transmit the push pulse that is focused on a divided ROI 31b at the transmission position 40e, and observes a shear wave that propagates in the direction indicated by an arrow 51b in the divided ROI 31b. The transmission control unit 173 controls to transmit the push pulse that is focused on a divided ROI 32b at the transmission position 40e, and observes a shear wave that propagates in the direction indicated by an arrow 52b in the divided ROI 32b. The transmission control unit 173 controls to transmit the push pulse that is focused on a divided ROI 31c at the transmission position 40f, and observes a shear wave that propagates in the direction indicated by an arrow 51c in the divided ROI 31c. The transmission control unit 173 controls to transmit the push pulse that is focused on a divided ROI 32c at the transmission position 40f, and observes a shear wave that propagates in the direction indicated by an arrow 52c in the divided ROI 32c. The transmission control unit 173 controls to transmit the push pulse that is focused on a divided ROI 31d at the transmission position 40g, and observes a shear wave that propagates in the direction indicated by an arrow 51d in the divided ROI 31*d*. The transmission control unit 173 controls to transmit the push pulse that is focused on a divided ROI 32*d* at the transmission position 40*g*, and observes a shear wave that propagates in the direction indicated by an arrow 52*d* in the divided ROI 32*d*. The transmission control unit 173 controls to transmit the push pulse that is focused on a divided ROI 31*e* at the transmission position 40*h*, and observes a shear wave that propagates in the direction indicated by an arrow 51*e* in the divided ROI 31*e*. The transmission control unit 173 controls to transmit the push pulse that is focused on a divided ROI 32*e* at the transmission position 40*h*, and observes a shear wave that propagates in the direction indicated by an arrow 52*e* in the divided ROI 32*e*.

As described, the ultrasonography apparatus 10 can generate stiffness image data of the ROI 30 based on a change of a displacement over time at each observed sample time by transmitting push pulses the focuses of which are different from each other to the respective divided ROIs.

Second Embodiment

Although a case in which a transmission condition is determined according to an instruction to set a scan mode or a frame rate has been explained, it is not limited thereto. For example, the ultrasonography apparatus 10 may set a transmission condition according to movement of the ultrasound probe 101.

Figure 9:
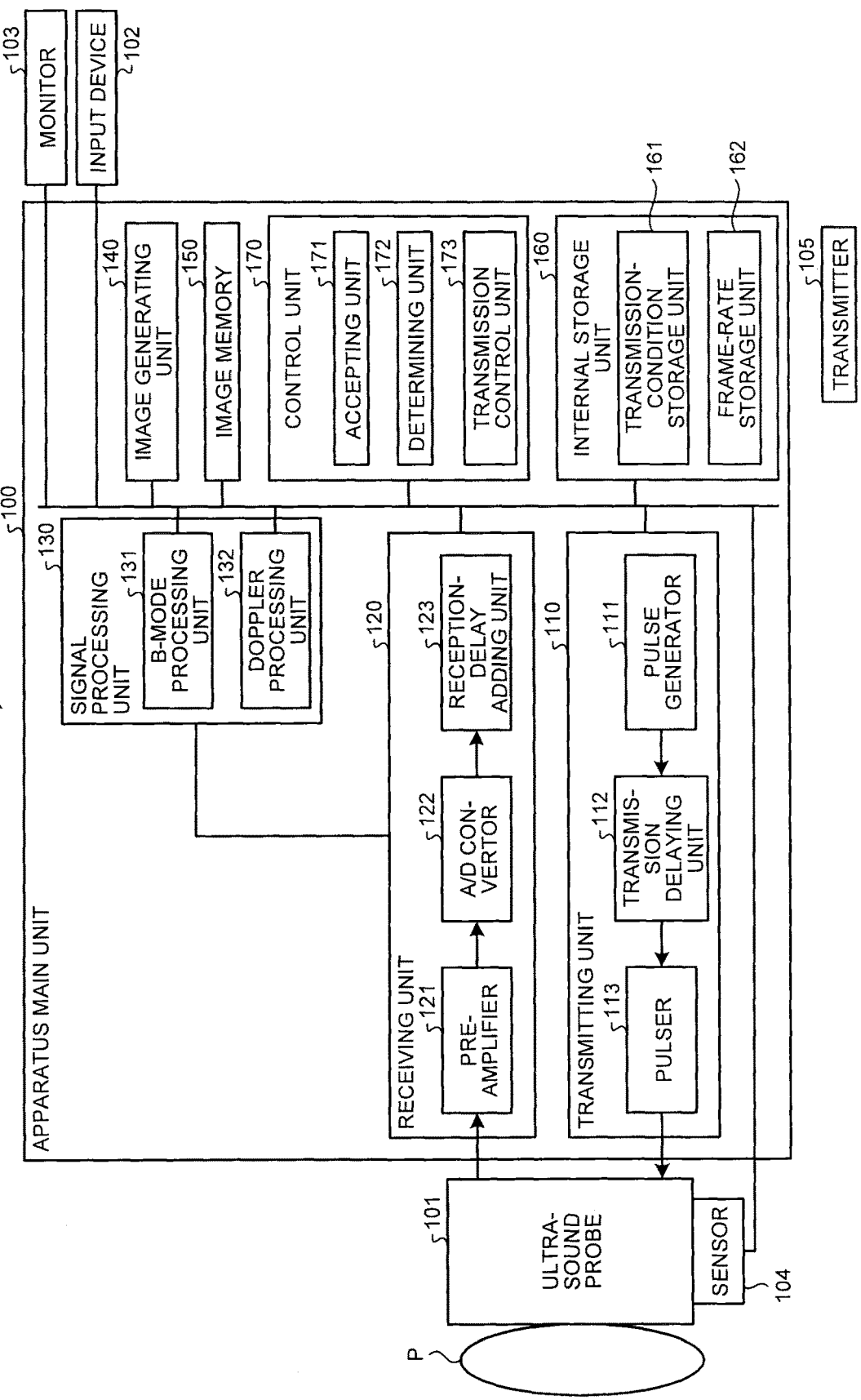
FIG. 9 is a block diagram showing a configuration example of an ultrasonography apparatus according to a second embodiment.

FIG. 9 is a block diagram showing a configuration example of the ultrasonography apparatus 10 according to a second embodiment. The ultrasonography apparatus 10 according to the second embodiment has a configuration similar to the ultrasonography apparatus 10 exemplified in FIG. 1, but differs in a point in which a sensor 104 and a transmitter 105 are further included, and a point in which the internal storage unit 160 stores a frame-rate storage unit 162. Therefore, in the second embodiment, the points different from the first embodiments are mainly explained, and as for functions similar to the components explained in the first embodiment, the same reference numerals are given thereto, and explanation thereof is omitted.

The sensor 104 and the transmitter 105 are devices to acquire position information of the ultrasound probe 101. For example, the sensor 104 is a magnetic sensor that is attached to the ultrasound probe 101. Furthermore, for example, the transmitter 105 is a device that is arranged at an arbitrary position, and forms a magnetic field outward from the device itself as a center. The sensor 104 and the transmitter 105 are one example of a detecting unit.

The sensor 104 detects a three-dimensional magnetic field that is formed by the transmitter 105. The sensor 104 then calculates a position of the device itself in a space the origin of which is the transmitter 105, based on information of the detected magnetic field. The sensor 104 calculates the acceleration of the ultrasound probe 101 based on the calculated position and time, as movement of the ultrasound probe 101. The sensor 104 then outputs the calculated acceleration of the ultrasound probe 101 to the accepting unit 171.

The frame-rate storage unit 162 stores a frame rate according to movement of the ultrasound probe 101. Data stored in the frame-rate storage unit 162 may be registered by an operator in advance, or may be preset.

FIG. 10 shows one example of data stored in the frame-rate storage unit 162 according to the second embodiment. As shown in FIG. 10, the frame-rate storage unit 162 stores data in which "movement of ultrasound probe" and "frame rate" are associated with each other. The "movement of ultrasound probe" indicates a speed of movement of the ultrasound probe 101 that is operated by an operator. Moreover, the "frame rate" indicates a frame rate that is determined according to movement of the ultrasound probe 101.

The accepting unit 171 accepts the movement of the ultrasound probe 101 detected by the sensor 104. For example, the accepting unit 171 accepts acceleration of the ultrasound probe 101 that is calculated by the sensor 104. The accepting unit 171 outputs the accepted acceleration of the ultrasound probe 101 to the determining unit 172.

The determining unit 172 determines a transmission condition according to movement of the ultrasound probe 101. For example, when accepting the acceleration of the ultrasound probe 101 from the accepting unit 171, the determining unit 172 compares the accepted acceleration with a predetermined threshold, to determine which one out of "fast", "intermediate", and "slow" the movement of the ultrasound probe 101 corresponds to.

The determining unit 172 then refers to the frame-rate storage unit 162, and acquires a frame rate according to the movement of the ultrasound probe 101. For example, the determining unit 172 acquires a frame rate "1.5 fps" when the movement of the ultrasound probe 101 is determined as "fast".

Subsequently, the determining unit 172 refers to the transmission-condition storage unit 161, and determines a transmission condition according to the frame rate acquired from the frame-rate storage unit 162. In this case, in the transmission-condition storage unit 161, transmission conditions according to frame rates are stored. For example, in the transmission-condition storage unit 161, data in which the frame rate "1.5 fps", the push-pulse transmission mode "one side", the push-pulse transmission interval "1.5 cm", and the observation-pulse transmission interval "1.5 mm" are associated with each other. When acquiring the frame rate "1.5 fps" from the frame-rate storage unit 162, the determining unit 172 acquires the push-pulse transmission mode "one side", the push-pulse transmission interval "1.5 cm", and the observation-pulse transmission interval "1.5 mm" that are associated with the frame rate "1.5 fps". The determining unit 172 then determines the acquired respective items as the transmission condition.

Figure 11:
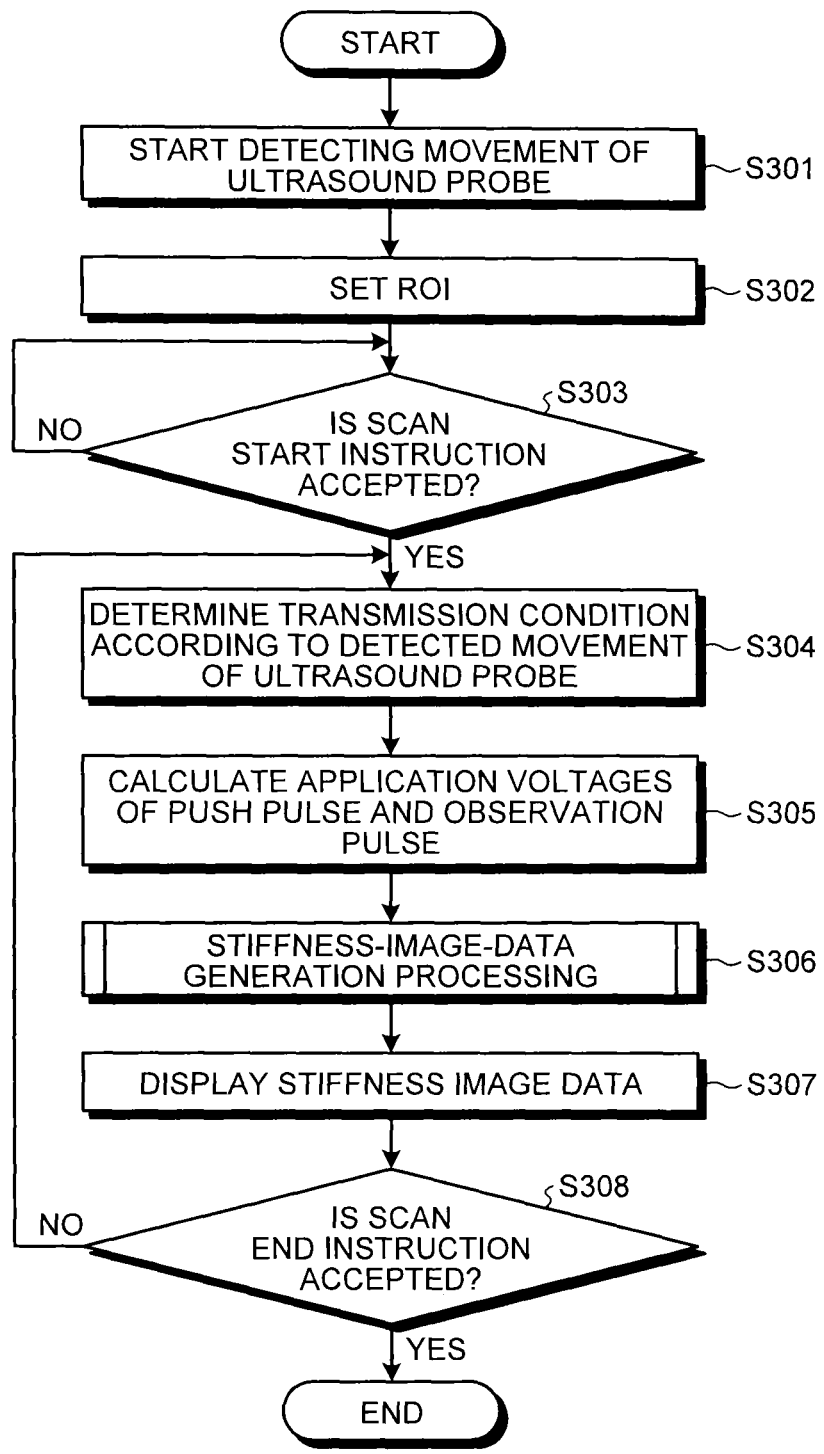
FIG. 11 is a flowchart of a processing procedure of the ultrasonography apparatus according to the second embodiment.

FIG. 11 is a flowchart of a processing procedure of the ultrasonography apparatus 10 according to the second embodiment. The processing procedure exemplified in FIG. 11 corresponds to the processing procedure after switched to the elastomode by an operator.

As shown in FIG. 11, in the ultrasonography apparatus 10 according to the second embodiment, when switched to the elastomode, the sensor 104 and the transmitter 105 start detection of movement of the ultrasound probe 101 (step S301). Thus, the accepting unit 171 accepts movement of the ultrasound probe 101.

The accepting unit 171 then accepts an instruction to set the ROI 30, and sets the ROI 30 according to the accepted instruction (step S302). Subsequently, the accepting unit 171 accepts an instruction to set a scan mode (step S303).

When the accepting unit 171 accepts a scan start instruction to start scanning (step S303: YES), the determining unit 172 determines a transmission condition according to the movement of the ultrasound probe 101 accepted by the accepting unit 171 (step S304). Note that the determining unit 172 waits in standby until the accepting unit 171 accepts a scan start instruction (step S303: NO).

Subsequently, the transmission control unit 173 calculates application voltages of the push pulse and the observation pulse (step S305). The transmission control unit 173 then performs stiffness-image-data generation processing based on the calculated application voltages of the push pulse and the observation pulse, and on the transmission condition (step S306). Explanation of this stiffness-image-data generation processing is the same as the explanation in FIG. 6, and therefore, is omitted.

By control by the transmission control unit 173, the monitor 103 displays stiffness image data of the ROI 30 (step S307). The transmission control unit 173 then shifts to step S304, and repeats generating stiffness image data until a scan end instruction is accepted (step S308: NO).

On the other hand, when a scan end instruction is accepted (step S308: YES), the transmission control unit 173 ends generation of stiffness image data.

As described, the ultrasonography apparatus 10 according to the second embodiment sets a transmission condition according to movement of the ultrasound probe 101. By this arrangement, for example, the ultrasonography apparatus 10 can increase a frame rate when the ultrasound probe 101 is frequently moving, and can decrease a frame rate when the ultrasound probe 101 is not moving.

Third Embodiment

Moreover, for example, the ultrasonography apparatus 10 may set a transmission condition according to the sensitivity of a region to be a subject of scanning.

Figure 12:
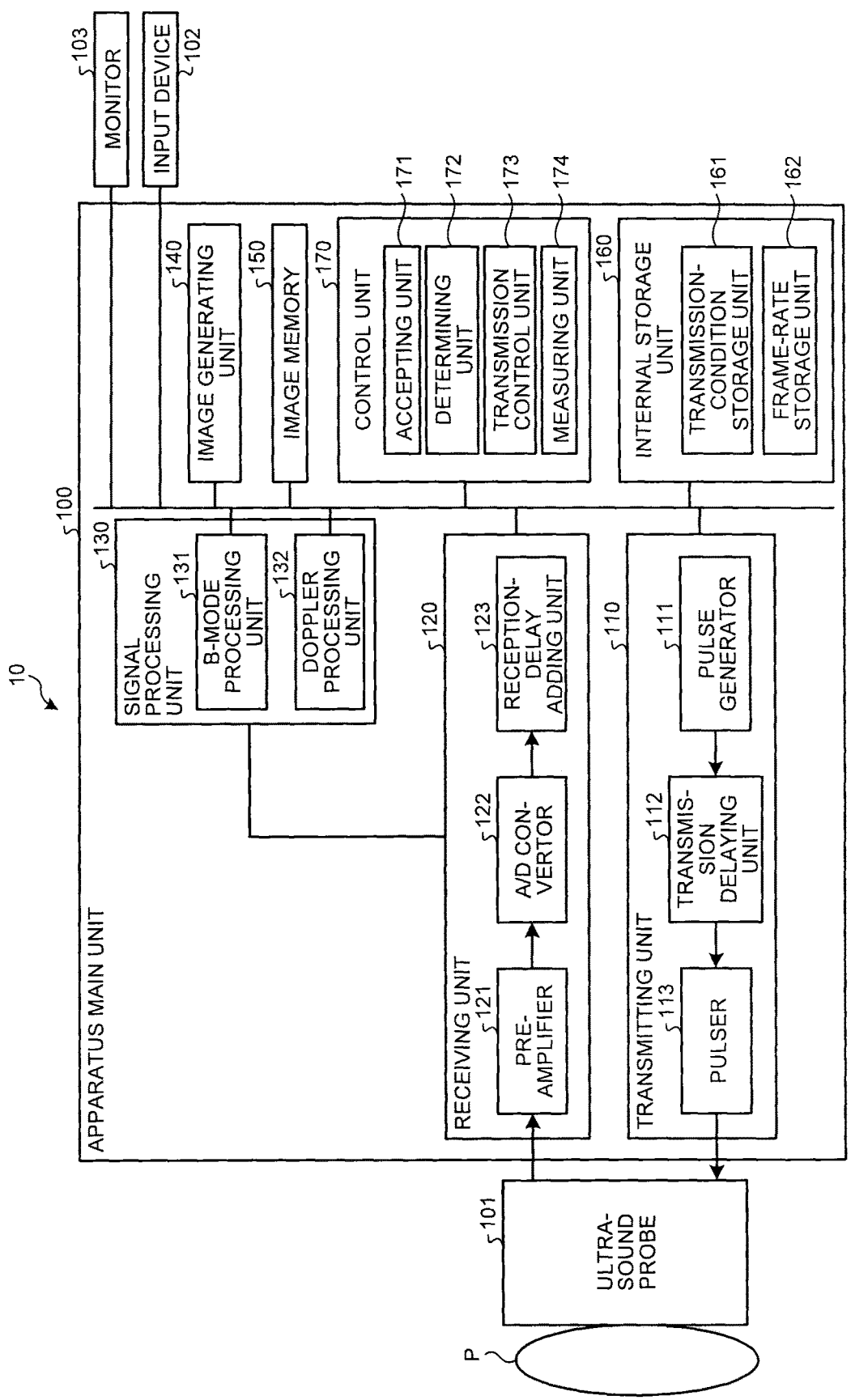
FIG. 12 is a block diagram showing a configuration example of an ultrasonography apparatus according to a third embodiment.

FIG. 12 is a block diagram showing a configuration example of the ultrasonography apparatus 10 according to a third embodiment. The ultrasonography apparatus 10 according to the third embodiment has a configuration similar to the ultrasonography apparatus 10 exemplified in FIG. 1, but differs in a point in which the control unit 170 includes a measuring unit 174, and a point in which the internal storage unit 160 stores the frame-rate storage unit 162. Therefore, in the third embodiment, the points different from the first embodiments are mainly explained, and as for functions similar to the components explained in the first embodiment, the same reference numerals are given thereto, and explanation thereof is omitted.

The frame-rate storage unit 162 according to the third embodiment stores a frame rate according to the sensitivity of a region to be a subject of scanning. Data stored in the frame-rate storage unit 162 may be registered by an operator in advance, or may be preset.

FIG. 13 shows one example of data stored in the frame-rate storage unit 162 according to the third embodiment. As shown in FIG. 13, the frame-rate storage unit 162 stores data in which a "B-mode S/N ratio" and a "frame rate" are associated with each other. The "B-mode S/N ratio" corresponds to a difference between a reception signal intensity at the time of transmission of an ultrasonic wave for B-mode image generation, and a reception signal intensity at the time when an ultrasonic wave for B-mode image generation.

The measuring unit 174 measures the sensitivity of a region to be a subject of scanning. For example, the measuring unit 174 measures a reflection intensity of a B-mode reception signal.

As one example, the measuring unit 174 measures an S/N ratio in B-mode. Specifically, the measuring unit 174 collects reception signals that are received at the ultrasound probe 101 in a state in which transmission of an ultrasonic wave for B-mode image generation is stopped. The measuring unit 174 then restart transmission of an ultrasonic wave for B-mode image generation, and measures a difference between the collected reception signal and a reception signal to the ultrasonic wave for B-mode image generation. Subsequently, the measuring unit 174 outputs a measurement result measured to the accepting unit 171.

The accepting unit 171 accepts a reflection intensity of a B-mode reception signal. For example, the accepting unit 171 accepts a measurement result that is measured by the measuring unit 174. The accepting unit 171 outputs the accepted measurement result to the determining unit 172.

The determining unit 172 determines a transmission condition according to the reflection intensity. For example, accepting a measurement result from the accepting unit 171, the determining unit 172 compares the accepted measurement result with a predetermined threshold, to determined which one out of "high", "intermediate", and "low" the S/N ratio in B-mode corresponds to.

The determining unit 172 then refers to the frame-rate storage unit 162, and acquires a frame rate according to the S/N ratio in B-mode. For example, when determining that the S/N ratio in B-mode is "high", the determining unit 172 acquires the frame rate "1.5 fps".

Subsequently, the determining unit 172 refers to the transmission-condition storage unit 161, and determines a transmission condition according to the frame rate acquired from the frame-rate storage unit 162. In this case, in the transmission-condition storage unit 161, transmission conditions according to frame rates are stored. For example, in the transmission-condition storage unit 161, data in which the frame rate "1.5 fps", the push-pulse transmission mode "one side", the push-pulse transmission interval "1.5 cm", and the observation-pulse transmission interval "1.5 mm" are associated with each other is stored. When acquiring the frame rate "1.5 fps" from the frame-rate storage unit 162, the determining unit 172 acquires the push-pulse transmission mode "one side", the push-pulse transmission interval "1.5 cm", and the observation-pulse transmission interval "1.5 mm" that are associated with the frame rate "1.5 fps". The determining unit 172 then determines the respective acquired items as a transmission condition.

Figure 14:
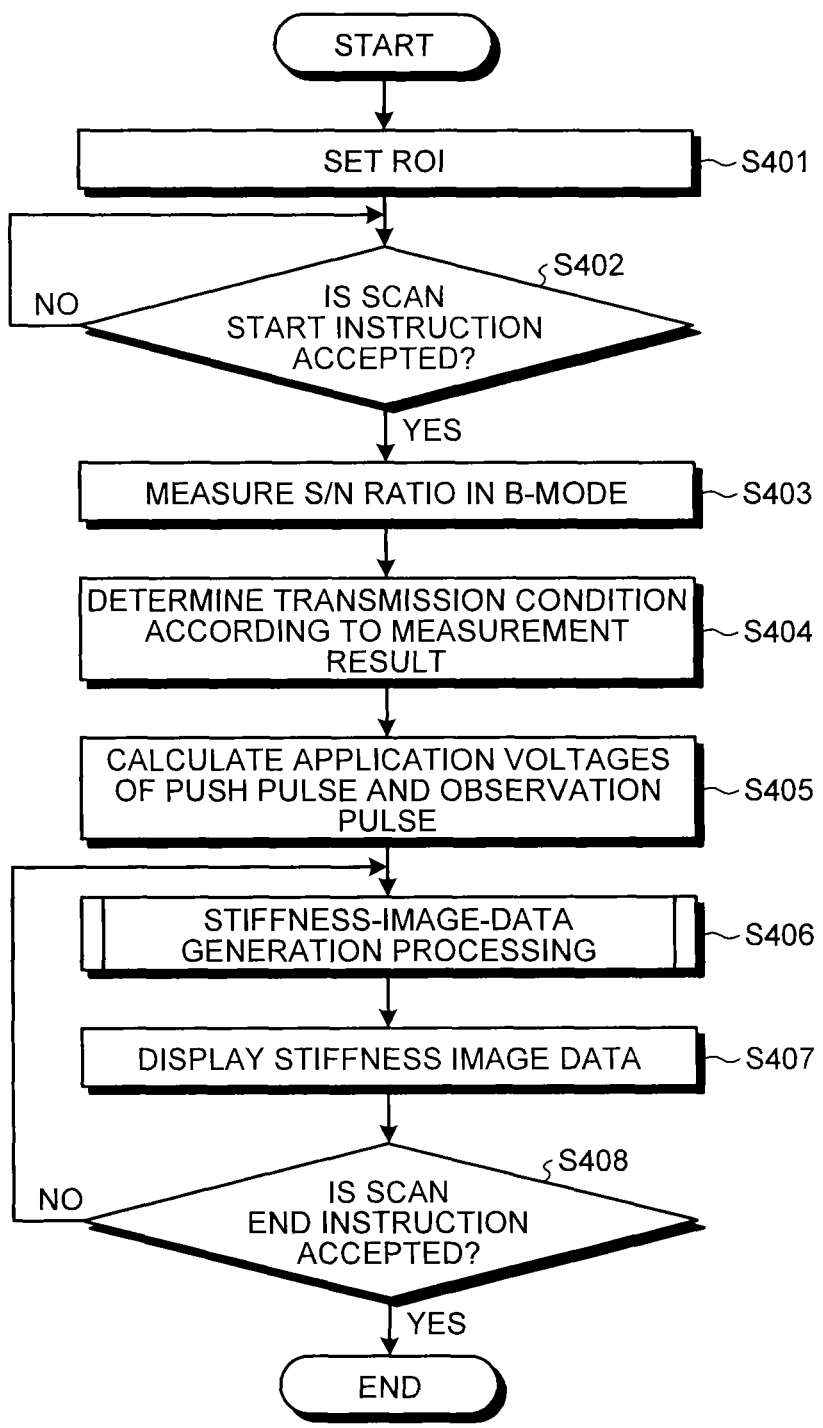
FIG. 14 is a flowchart of a processing procedure of the ultrasonography apparatus according to the third embodiment.

FIG. 14 is a flowchart of a processing procedure of the ultrasonography apparatus 10 according to the third embodiment. The processing procedure exemplified in FIG. 14 corresponds to a processing procedure after switched to the elastomode by an operator.

As shown in FIG. 14, in the ultrasonography apparatus 10 according to the third embodiment, when switched to the elastomode, the accepting unit 171 accepts an instruction to set the ROI 30, and sets the ROI 30 according to the accepted instruction (step S401).

When the accepting unit 171 accepts a scan start instruction (step S402: YES), the measuring unit 174 measures an S/N ratio in B-mode (step S403). Note that the measuring unit 174 waits in standby until the accepting unit 171 accepts a scan start instruction (step S402: NO).

Subsequently, the determining unit 172 determines a transmission condition according to a measurement result (step S404). The transmission control unit 173 calculates application voltages of the push pulse and the observation pulse (step S405). The transmission control unit 173 then performs stiffness-image-data generation processing based on the calculated application voltages of the push pulse and the observation pulse, and on the transmission condition (step S406). Explanation of this stiffness-image-data generation processing is the same as the explanation in FIG. 6, and therefore, is omitted.

By control by the transmission control unit 173, the monitor 103 displays stiffness image data of the ROI 30 (step S407). The transmission control unit 173 then shifts to step S406, and repeats generating stiffness image data until a scan end instruction is accepted (step S408: NO).

On the other hand, when a scan end instruction is accepted (step S408: YES), the transmission control unit 173 ends generation of stiffness image data.

As described, the ultrasonography apparatus 10 according to the third embodiment sets a transmission condition according to the sensitivity of a region to be a subject of scanning. By this arrangement, for example, the ultrasonography apparatus 10 can lower a frame rate when the S/N ratio in B-mode is low, giving a priority to the image quality, and can increase a frame rate when the S/N ratio in B-mode is high.

Modification of Third Embodiment

In the third embodiment, not limited to the S/N ratio in B-mode, a displacement amount by the push pulse may be measured, and a transmission condition may be determined based on the measured displacement amount, for example.

FIG. 15 shows one example of data stored in the frame-rate storage unit 162 according to a modification of the third embodiment. As shown in FIG. 15, the frame-rate storage unit 162 stores data in which a "displacement amount" and a "frame rate" are associated with each other. The "displacement amount" indicates an amount of displacement caused by the push pulse transmitted to the center of the ROI 30.

The measuring unit 174 according to the modification of the third embodiment measures, for example, a displacement amount caused by the push pulse.

As one example, the measuring unit 174 transmits the push pulse to the center of the ROI 30, and observes a displacement caused by the push pulse at the transmitted position. The measuring unit 174 then outputs the observed displacement amount to the accepting unit 171.

The accepting unit 171 accepts the displacement amount caused by the push pulse. For example, the accepting unit 171 accepts the displacement amount measured by the measuring unit 174. The accepting unit 171 then outputs the accepted displacement amount to the determining unit 172.

The determining unit 172 determines a transmission condition according to the displacement amount caused by the push pulse. For example, when accepting the displacement amount caused by the push pulse from the accepting unit 171, the determining unit 172 refers to the frame-rate storage unit 162, and acquires a frame rate corresponding to the accepted displacement amount. Subsequently, the determining unit 172 refers to the transmission-condition storage unit 161, and determines a transmission condition according to the frame rate acquired from the frame-rate storage unit 162.

Figure 16:
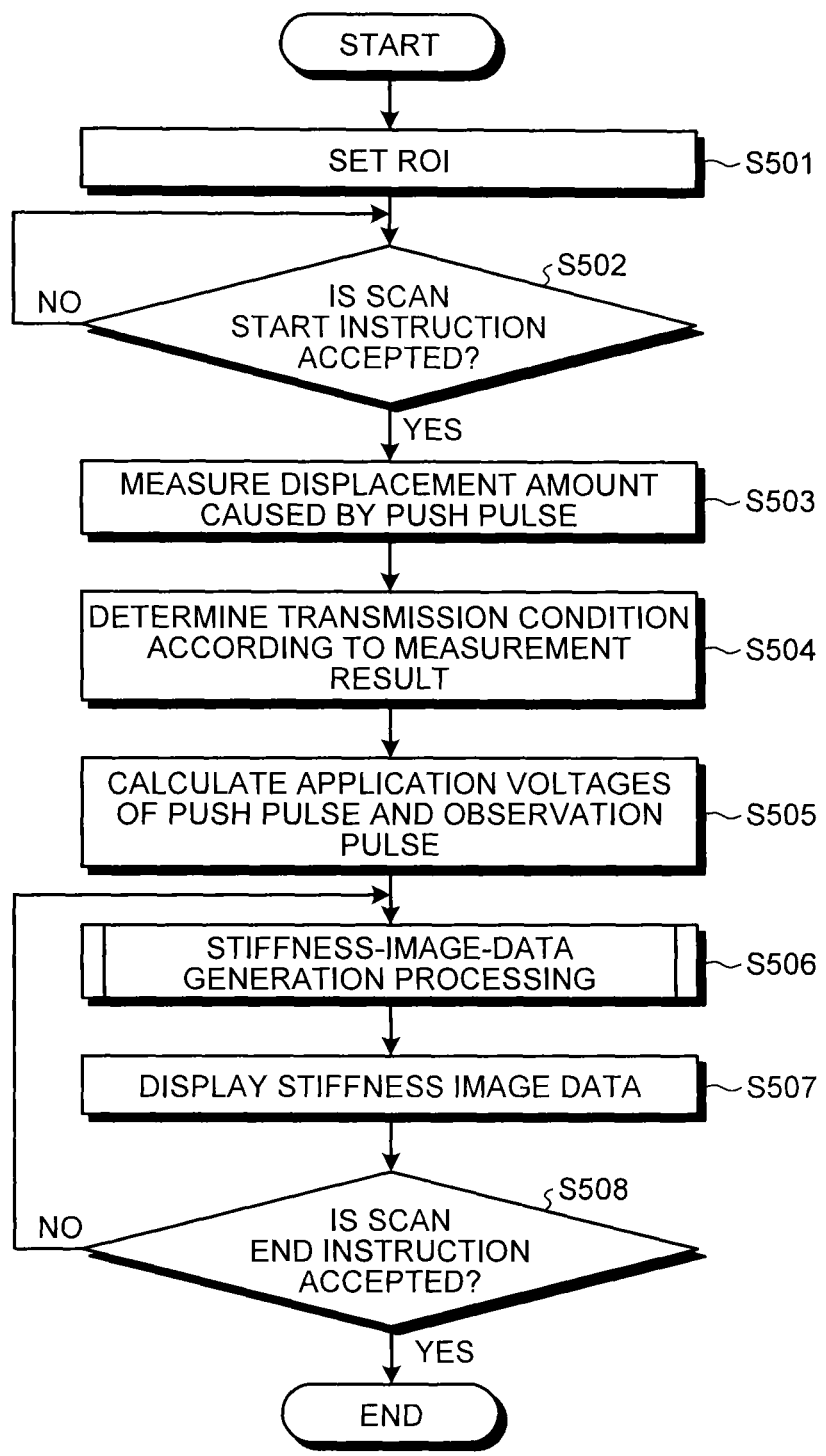
FIG. 16 is a flowchart of a processing procedure of the ultrasonography apparatus according to the modification of the third embodiment.

FIG. 16 is a flowchart of a processing procedure of the ultrasonography apparatus 10 according to the modification of the third embodiment. The processing procedure exemplified in FIG. 16 corresponds to a processing procedure after switched to the elastomode by an operator.

As shown in FIG. 16, in the ultrasonography apparatus 10 according to the third embodiment, when switched to the elastomode, the accepting unit 171 accepts an instruction to set the ROI 30, and sets the ROI 30 according to the accepted instruction (step S501).

When the accepting unit 171 accepts a scan start instruction (step S502: YES), the measuring unit 174 measures a displacement amount caused by the push pulse (step S503). Note that the measuring unit 174 waits in standby until a scan start instruction is accepted by the accepting unit 171 (step S502: NO).

Subsequently, the determining unit 172 determines a transmission condition according to a measurement result (step S504). The transmission control unit 173 calculates application voltages of the push pulse and the observation pulse (step S505). The transmission control unit 173 then performs stiffness-image-data generation processing based on the calculated application voltages of the push pulse and the observation pulse, and on the transmission condition (step S506). Explanation of this stiffness-image-data generation processing is the same as the explanation in FIG. 6, and therefore, is omitted.

By control by the transmission control unit 173, the monitor 103 displays stiffness image data of the ROI 30 (step S507). The transmission control unit 173 then shifts to step S506, and repeats generating stiffness image data until a scan end instruction is accepted (step S508: NO).

On the other hand, when a scan end instruction is accepted (step S508: YES), the transmission control unit 173 ends generation of stiffness image data.

As described, the ultrasonography apparatus 10 according to the third embodiment sets a transmission condition according to the sensitivity of a region to be a subject of scanning. By this arrangement, for example, the ultrasonography apparatus 10 can lower a frame rate when a displacement is not likely to be caused by the push pulse, giving a priority to the image quality, and can increase a frame rate when a displacement is caused sufficiently.

Another Embodiment

The respective components in the respective apparatuses shown in the explanation of the first to the second embodiments are of functional concept, and it is not necessarily required to be physically configured as shown in the drawings. Specifically, a specific form of distribution and integration of the respective devices are not limited to the ones shown in the drawings, and it can be configured such that all or a part thereof is functionally or physically distributed or integrated in arbitrary units according to various kinds of load and usage condition and the like. Furthermore, as for the respective processing functions of the respective devices, all or an arbitrary part thereof can be implemented by a central processing unit (CPU) and a computer program that is analyzed and executed by the CPU, or can be implemented as hardware by wired logic.

Figure 17:
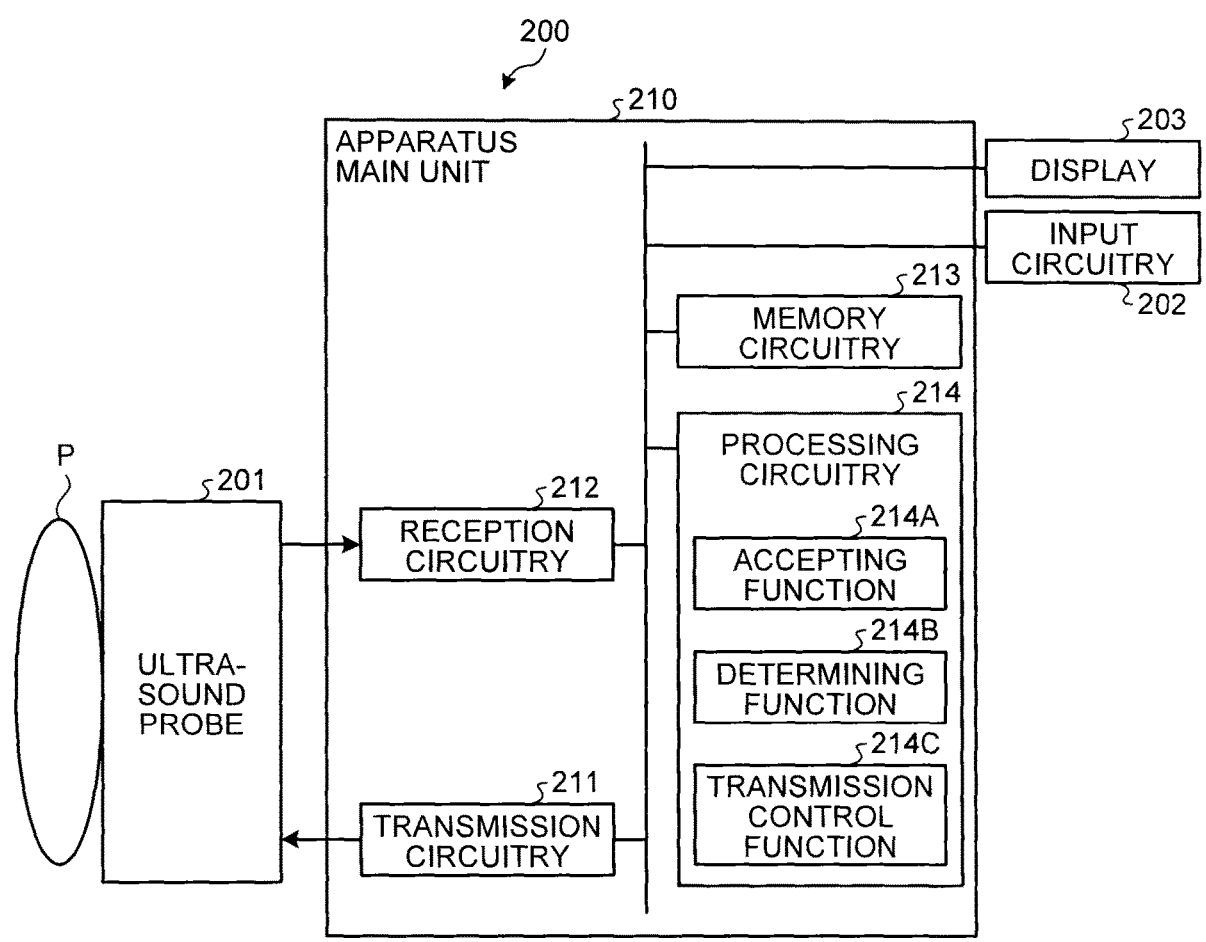
FIG. 17 is a block diagram showing a configuration example of an ultrasonography apparatus according to another embodiment.

For example, the ultrasonography apparatus 10 shown in FIG. 1 may be configured as shown in FIG. 17. FIG. 17 is a block diagram showing a configuration example of an ultrasonography apparatus according to another embodiment.

As shown in FIG. 17, an ultrasonography apparatus 200 includes an ultrasound probe 201, input circuitry 202, a display 203, and an apparatus main unit 210. The ultrasound probe 201, the input circuitry 202, and the display 203 correspond to the ultrasound probe 101, the input device 102, and the monitor 103 shown in FIG. 1, respectively.

The apparatus main unit 210 includes a transmission circuitry 211, reception circuitry 212, memory circuitry 213, and processing circuitry 214. The transmission circuitry 211 and the reception circuitry 212 correspond to the transmitting unit 110 and the receiving unit 120 shown in FIG. 1, respectively. The transmission circuitry 211 is an example of transmission circuitry in the accompanying claims.

Moreover, the memory circuitry 213 corresponds to the image memory 150 and the internal storage unit 160 shown in FIG. 1. That is, the memory circuitry 213 stores data stored in the image memory 150 and the internal storage unit 160.

Furthermore, the processing circuitry 214 corresponds to the signal processing unit 130, the image generating unit 140, and the control unit 170 shown in FIG. 1. That is, the processing circuitry 214 performs processing performed by the signal processing unit 130, the image generating unit 140, and the control unit 170. The processing circuitry 214 is an example of processing circuitry in the accompanying claims.

The processing circuitry 214 performs an accepting function 214A, a determining function 214B, and a transmission control function 214C. The accepting function 214A is a function implemented by the accepting unit 171 illustrated in FIG. 1. The determining function 214B is a function implemented by the determining unit 172 illustrated in FIG. 1. The transmission control function 214C is a function implemented by the transmission control unit 173 illustrated in FIG. 1.

For example, each of the respective processing functions performed by the accepting function 214A, the determining function 214B, and the transmission control function 214C, which are components of the processing circuitry 214 illustrated in FIG. 17, is stored in the memory circuitry 213 in a form of a computer-executable program. The processing circuitry 214 is a processor that loads programs from the memory circuitry 213 and executes the programs so as to implement the respective functions corresponding to the programs. In other words, the processing circuitry 214 that has loaded the programs has the functions illustrated in the processing circuitry 214 in FIG. 17. That is, the processing circuitry 214 loads a program corresponding to the accepting function 214A from the memory circuitry 213 and executes the program so as to perform the same processing as that of the accepting unit 171. The processing circuitry 214 loads a program corresponding to the determining function 214B from the memory circuitry 213 and executes the program so as to perform the same processing as that of the determining unit 172. The processing circuitry 214 loads a program corresponding to the transmission control function 214C from the memory circuitry 213 and executes the program so as to perform the same processing as that of the transmission control unit 173.

For example, Steps S101 to S103 illustrated in FIG. 5 are steps that is implemented by the processing circuitry 214 loading the program corresponding to the accepting function 214A from the memory circuitry 213 and executing the program. Step S104 illustrated in FIG. 5 is a step that is implemented by the processing circuitry 214 loading the program corresponding to the determining function 214B from the memory circuitry 213 and executing the program. Step S108 illustrated in FIG. 5 is a step that is implemented by the processing circuitry 214 loading the program corresponding to the transmission control function 214C from the memory circuitry 213 and executing the program.

In FIG. 17, the processing functions performed by the accepting function 214A, the determining function 214B, and the transmission control function 214C are described as being implemented in the single processing circuit. The functions, however, may be implemented by configuring a processing circuit by combining a plurality of separate processors and causing each of the processors to execute a program.

The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the present embodiment are not limited to a case in which each of the processors is configured as a single circuit. A plurality of separate circuits may be combined as one processor that implements the respective functions. Furthermore, the components illustrated in FIG. 17 may be integrated into one processor that implements the respective functions.

The respective circuitry exemplified in FIG. 17 may be distributed or integrated as appropriate. For example, the processing circuitry 214 may be configured with a circuitry having a function of the signal processing unit 130, and a circuitry having functions of the image generating unit 140 and the control unit 170, in a distributed manner.

Moreover, the respective processing in the ultrasonography apparatus explained in the first to the third embodiments can be implemented by executing an ultrasonic imaging program prepared in advance. The ultrasonic imaging program can be distributed through a network such as the Internet. Furthermore, the ultrasonic imaging program can be stored in a computer-readable non-temporary recording medium such as a hard disk, a flexible disk (FD), a compact-disc read-only memory (CD-ROM), a magneto optical disk (MO), and a digital versatile disc (DVD), and can be executed by being read by a computer from the non-temporary recording medium.

According to at least one of the embodiments explained above, a stiffness image having high image quality can be obtained by a simple operation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonography apparatus, comprising:
    transmission circuitry configured to
        cause an ultrasound probe to transmit a push pulse to cause a displacement in a tissue of a living body based on an acoustic radiation force, and
        cause the ultrasound probe to transmit observation pulses to observe the displacement of the tissue of the living body in a predetermined scan region, the displacement caused based on the push pulse;
    a storage configured to store a table which associates an acquisition frequency of an image, a transmission mode indicating whether to transmit the push pulse to one end or both ends of the scan region, a push-pulse transmission interval indicating intervals in an azimuth direction of push pulses, and an observation-pulse transmission interval indicating intervals in an azimuth direction of observation-pulses with each other, wherein the acquisition frequency of the image corresponds to the predetermined scan region and is based on a reflected wave signal acquired by the ultrasound probe by transmission and reception of the observation pulses; and processing circuitry configured to
   accept a setting instruction to set the acquisition frequency,
   acquire, from the table, the transmission mode, the push-pulse transmission interval, and the observation-pulse transmission interval corresponding to the acquisition frequency set by the setting instruction, and
   control the transmission circuitry based on the acquired transmission mode, push-pulse transmission interval, and observation-pulse transmission interval.

2. The ultrasonography apparatus according to claim 1, wherein
   the processing circuitry is further configured to accept one of a setting instruction to perform a single time of imaging and a setting instruction to perform a plurality of times of imaging, as the setting instruction.

3. The ultrasonography apparatus according to claim 1, wherein
   the processing circuitry is further configured to determine, according to the acquisition frequency, whether to transmit the push pulse to one end of the scan region, or to transmit the push pulse to both ends of the scan region.

4. The ultrasonography apparatus according to claim 2, wherein
   the processing circuitry is further configured to determine, according to the acquisition frequency, whether to transmit the push pulse to one end of the scan region, or to transmit the push pulse to both ends of the scan region.

5. The ultrasonography apparatus according to claim 1, wherein
   the processing circuitry is further configured to determine, according to the acquisition frequency, a number of transmission positions of the push pulse that is transmitted to the scan region.

6. The ultrasonography apparatus according to claim 2, wherein
   the processing circuitry is further configured to determine, according to the acquisition frequency, a number of transmission positions of the push pulse that is transmitted to the scan region.

7. The ultrasonography apparatus according to claim 1, wherein
   the processing circuitry is further configured to determine, according to the acquisition frequency, a number of focuses of the push pulse that is transmitted to the scan region.

8. The ultrasonography apparatus according to claim 2, wherein
   the processing circuitry is further configured to determine, according to the acquisition frequency, a number of focuses of the push pulse that is transmitted to the scan region.

9. The ultrasonography apparatus according to claim 1, wherein
   the processing circuitry is further configured to determine a second azimuth interval of the observation pulses in an azimuth direction, according to the acquisition frequency.

10. The ultrasonography apparatus according to claim 2, wherein
    the processing circuitry is further configured to determine a second azimuth interval of the observation pulses, according to the acquisition frequency.

11. The ultrasonography apparatus according to claim 1, wherein
    the processing circuitry is further configured to determine application voltages of the push pulse and the observation pulses, based on a transmission condition.

12. The ultrasonography apparatus according to claim 2, wherein
    the processing circuitry is further configured to determine application voltages of the push pulse and the observation pulses, based on a transmission condition.

13. The ultrasonography apparatus according to claim 1, wherein
    the processing circuitry is further configured to receive information of movement of the ultrasound probe, accept the information of the movement of the ultrasound probe as the setting instruction, and determine a transmission condition according to the information of the movement of the ultrasound probe.

14. The ultrasonography apparatus according to claim 2, wherein
    the processing circuitry is further configured to receive information of movement of the ultrasound probe, accept the information of the movement of the ultrasound probe as the setting instruction, and determine a transmission condition according to the information of the movement of the ultrasound probe.

15. The ultrasonography apparatus according to claim 1, wherein
    the processing circuitry is further configured to measure a reflection intensity of a reception signal of B-mode, accept the measured reflection intensity as the setting instruction, and determine a transmission condition according to the reflection intensity.

16. The ultrasonography apparatus according to claim 2, wherein
    the processing circuitry is further configured to measure a reflection intensity of a reception signal of B-mode, accept the measured reflection intensity as the setting instruction, and determine a transmission condition according to the reflection intensity.

17. The ultrasonography apparatus according to claim 1, wherein
    the processing circuitry is further configured to measure the displacement caused by the push pulse, accept the measured displacement as the setting instruction, and determine a transmission condition according to the displacement.

18. The ultrasonography apparatus according to claim 2, wherein
    the processing circuitry is further configured to measure the displacement caused by the push pulse, accept the measured displacement as the setting instruction, and determine a transmission condition according to the displacement.

19. The ultrasonography apparatus of claim 1, wherein the processing circuitry is further configured to accept as the setting instruction to set the acquisition frequency: (1) an instruction to set a one shot mode for acquiring one image or (2) an instruction to set a frame rate in a successive scan mode for repeatedly acquiring images.

* * * * *